United States Patent
Yeung et al.

(10) Patent No.: US 11,096,747 B2
(45) Date of Patent: *Aug. 24, 2021

(54) SURGICAL ROBOTIC DEVICES AND SYSTEMS FOR USE IN PERFORMING MINIMALLY INVASIVE AND NATURAL ORIFICE TRANSLUMINAL ENDOSCOPIC SURGICAL ACTIONS

(71) Applicant: Bio-Medical Engineering (HK) Limited, Hong Kong (CN)

(72) Inventors: Chung Kwong Yeung, Hong Kong (CN); Wing Fai Lam, Hong Kong (CN); Wai Lik Alik Chan, Hong Kong (CN)

(73) Assignee: Bio-Medical Engineering (HK) Limited, Hong Kong (CN)

( * ) Notice: Subject to any disclaimer, the term of this patent is extended or adjusted under 35 U.S.C. 154(b) by 246 days.

This patent is subject to a terminal disclaimer.

(21) Appl. No.: 16/172,389

(22) Filed: Oct. 26, 2018

(65) Prior Publication Data

US 2019/0060010 A1 Feb. 28, 2019

Related U.S. Application Data

(63) Continuation of application No. 15/786,294, filed on Oct. 17, 2017, now Pat. No. 10,166,081, which is a
(Continued)

(51) Int. Cl.
*A61B 34/30* (2016.01)
*A61B 18/14* (2006.01)

(52) U.S. Cl.
CPC .......... *A61B 34/30* (2016.02); *A61B 18/1445* (2013.01); *A61B 2034/302* (2016.02); *A61B 2034/303* (2016.02); *A61B 2034/305* (2016.02)

(58) Field of Classification Search
CPC .......... A61B 18/1445; A61B 2034/302; A61B 2034/303; A61B 2034/305; A61B 34/30
See application file for complete search history.

(56) References Cited

U.S. PATENT DOCUMENTS 5,792,135 A * 8/1998 Madhani .......... A61B 17/00234
606/1
6,312,435 B1 * 11/2001 Wallace ................ A61B 34/70
606/130
(Continued)

FOREIGN PATENT DOCUMENTS

CN 104783844 A 7/2015
CN 104983469 A 10/2015
(Continued)

OTHER PUBLICATIONS

Office Action dated Mar. 9, 2020 in connection with Singaporean Application No. 10201809837X, 10 pages.
(Continued)

*Primary Examiner* — Michael F Peffley
(74) *Attorney, Agent, or Firm* — Baker & McKenzie LLP

(57) ABSTRACT

Example embodiments relate to surgical systems and methods. System includes an end-effector assembly and arm assembly. End-effector assembly includes an instrument assembly and wrist assembly. Instrument assembly includes an instrument and instrument driven portion. Instrument driven portion includes an instrument connection portion and instrument driven gear. Instrument connection portion connects the instrument driven gear to the instrument. Wrist assembly includes a wrist driven gear and wrist body, which connects the wrist driven gear to the instrument assembly. Arm assembly includes a wrist connector portion and integrated motors. Arm assembly attaches to and detaches from the wrist assembly. When the arm assembly is attached to the wrist assembly, the instrument driven gear and wrist driven
(Continued)

gear are drivable to rotate by the integrated motors. When the arm assembly is detached from the wrist assembly, the instrument driven gear and wrist driven gear are not drivable to rotate by the integrated motors.

26 Claims, 11 Drawing Sheets

Related U.S. Application Data continuation of application No. 15/340,699, filed on Nov. 1, 2016, now Pat. No. 9,827,058.

(56) References Cited

U.S. PATENT DOCUMENTS

| | | | |
|---|---|---|---|
| 7,422,592 B2* | 9/2008 | Morley | A61B 18/1445 606/51 |
| 9,010,214 B2 | 4/2015 | Markvicka | |
| 2007/0123855 A1 | 5/2007 | Morley et al. | |
| 2008/0043122 A1 | 2/2008 | Manzo et al. | |
| 2008/0046122 A1 | 2/2008 | Manzo et al. | |
| 2008/0108443 A1 | 5/2008 | Jinno et al. | |
| 2010/0016853 A1 | 1/2010 | Burbank | |
| 2011/0144657 A1 | 6/2011 | Fish et al. | |
| 2011/0167611 A1 | 7/2011 | Williams | |
| 2013/0131695 A1* | 5/2013 | Scarfogliero | A61B 34/30 606/130 |
| 2013/0144395 A1 | 6/2013 | Stefanchik et al. | |
| 2015/0297299 A1* | 10/2015 | Yeung | A61B 1/0016 600/102 |
| 2016/0157948 A1 | 6/2016 | Yeung | |
| 2017/0042623 A1 | 2/2017 | Yeung | |
| 2017/0042624 A1 | 2/2017 | Yeung | |

FOREIGN PATENT DOCUMENTS

| | | |
|---|---|---|
| WO | 95/10241 A2 | 4/1995 |
| WO | 2010009223 A2 | 1/2010 |
| WO | 2014-085718 A1 | 6/2014 |
| WO | 2016165004 A1 | 10/2016 |

OTHER PUBLICATIONS

First Examination Report dated Jun. 29, 2020 in connection with Indian Application No. 201817037445, 6 pages.

* cited by examiner

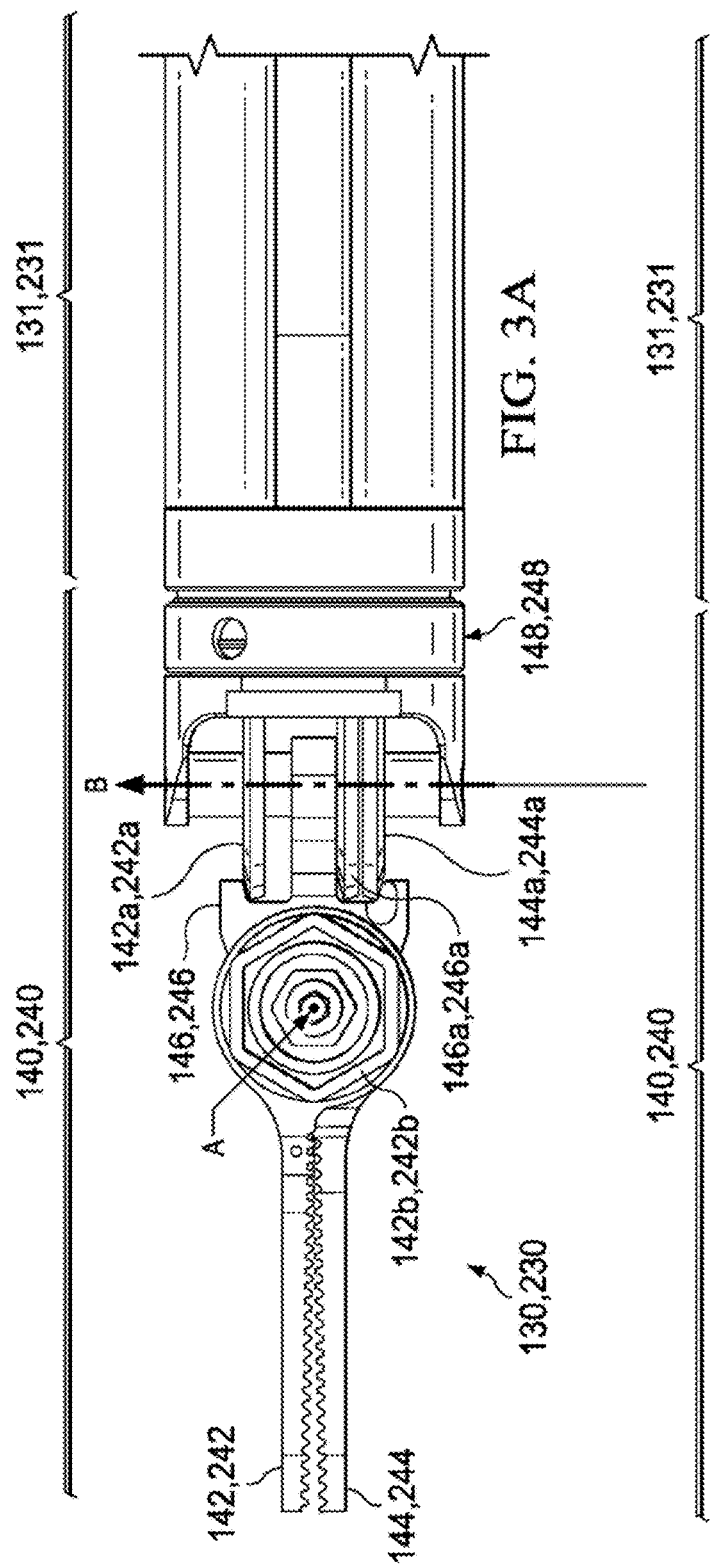

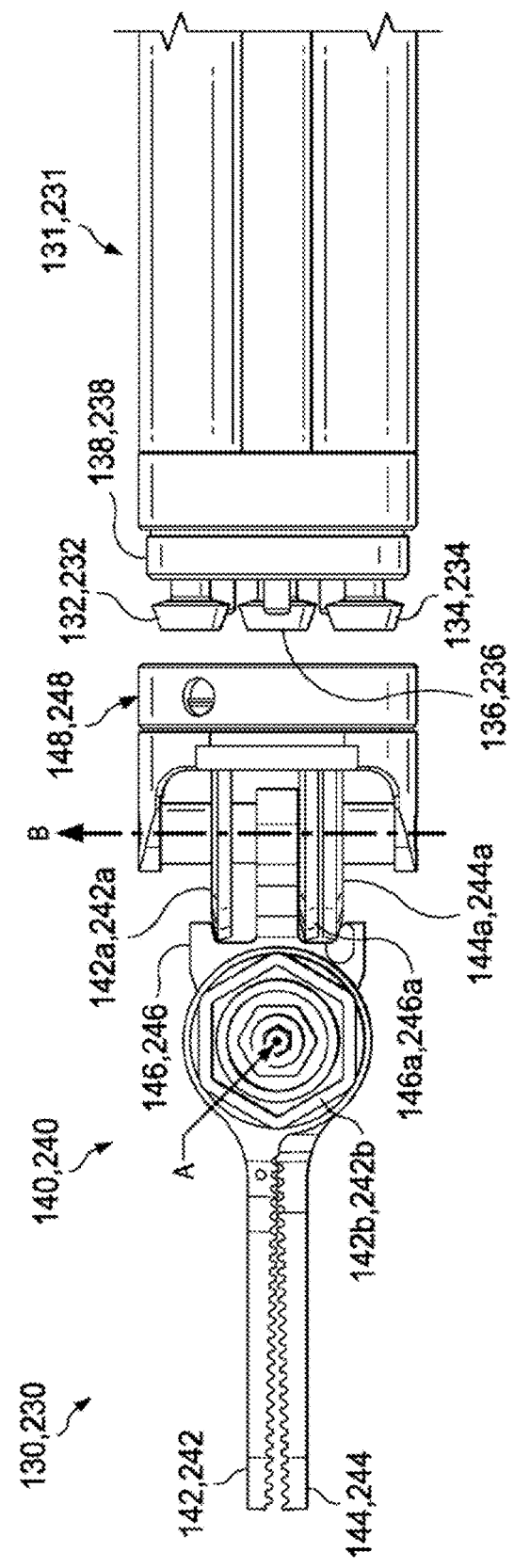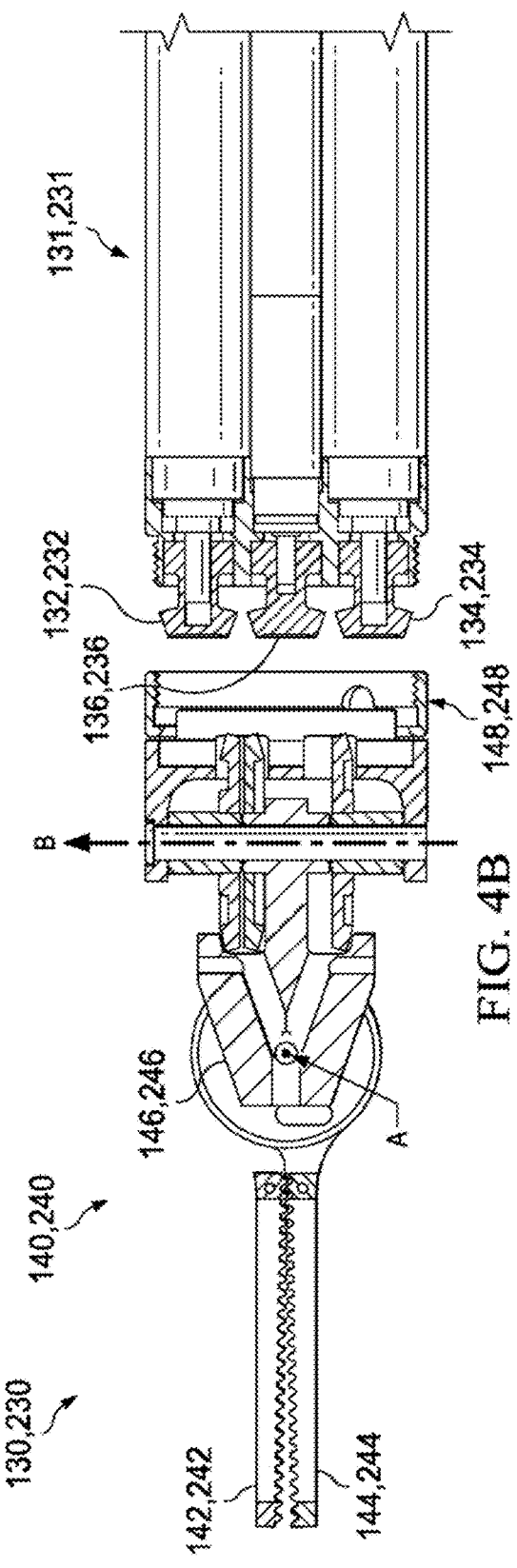
FIG. 4A
FIG. 4B

SURGICAL ROBOTIC DEVICES AND SYSTEMS FOR USE IN PERFORMING MINIMALLY INVASIVE AND NATURAL ORIFICE TRANSLUMINAL ENDOSCOPIC SURGICAL ACTIONS

CROSS-REFERENCE TO RELATED APPLICATIONS

This application is a continuation of and claims priority to U.S. patent application Ser. No. 15/786,294 (filed on Oct. 17, 2017 and granted as U.S. Pat. No. 10,166,081, which is a continuation of U.S. patent application Ser. No. 15/340,699 (filed on Nov. 1, 2016 and granted as U.S. Pat. No. 9,827,058)). The contents of the aforementioned priority application is hereby incorporated by reference in their entirety

BACKGROUND

The present disclosure relates generally to systems, devices, and methods for use in performing surgical procedures, and more specifically, relates to surgical robotic systems, devices, and methods for use in performing surgical actions including, but not limited to, minimally invasive surgical procedures (MIS) and natural orifice transluminal endoscopic surgical procedures (NOTES).

Conventionally, surgical procedures performed in a body cavity of a patient, such as the abdominal cavity, required one or more large access incisions to a patient in order for the surgical team to perform a surgical action. With advancements in medical science and technology, such conventional surgical procedures have been largely replaced by minimally invasive surgery (MIS) procedures and, where applicable, natural orifice transluminal endoscopic surgical procedures (NOTES). Recent developments in respect to computer-assisted and/or robotic surgical technology have contributed to advancements in the MIS and NOTES fields, including the ability to translate a surgeon's desired surgical actions into precise movements of surgical instruments inside a body cavity of a patient.

BRIEF SUMMARY

Despite recent developments in modern medical science and technology, it is recognized in the present disclosure that one or more problems are encountered in modern surgical technology and methodology. For example, a typical MIS procedure requires multiple incisions to a patient in order to allow access via the incisions for the insertion of a camera and various other laparoscopic instruments into the body cavity of the patient.

As another example, surgical robotic devices oftentimes encounter difficulties during surgical procedures due to insufficient anchoring and/or reactive forces to stabilize against forces that are desired and/or necessary to be applied during surgical actions.

It is also recognized in the present disclosure that surgical robotic systems face difficulties in providing an instrument, such as a cutting or gripping instrument attached to the end of a surgical robotic arm, with access to all or even most parts, areas, and/or quadrants of abdominal cavity of a patient. That is, after the surgical robotic arm is inserted in the abdominal cavity of the patient and ready to perform a surgical action, the instrument attached to the end of the surgical robotic arm is typically limited to access only certain parts, areas, and quadrants of the abdominal cavity of the patient.

In yet another example, known surgical robotic systems typically provide only between one to two surgical robotic arms per access or opening (such as an incision or a natural orifice) of the patient. In this regard, one or more additional incisions will be required for the insertion of a camera and various laparoscopic instruments into the abdominal cavity of the patient.

Present example embodiments relate generally to systems, devices, and methods for addressing one or more problems in surgical robotic systems, devices, and methods, including those described above and herein.

In an exemplary embodiment, a surgical arm assembly is disclosed. The surgical arm assembly may include an end-effector assembly and an arm assembly. The end-effector assembly may include a first instrument assembly and a wrist assembly. The first instrument assembly may include a first instrument having a proximal end and a distal end. The first instrument assembly may also include a first instrument driven portion having a first instrument connection portion and a first instrument driven gear. The first instrument connection portion may connect the first instrument driven gear to the proximal end of the first instrument in such a way that, when the first instrument driven gear is driven to rotate, the distal end of the first instrument is driven to rotate relative to a first central axis. The wrist assembly may be connected to the first instrument assembly. The wrist assembly may include a wrist driven gear and a wrist body. The wrist body may connect the wrist driven gear to the first instrument assembly. When the wrist driven gear is driven to rotate, the first instrument assembly is driven to rotate relative to a second central axis. The first central axis may be orthogonal to the second central axis. The first central axis may be non-coplanar to the first central axis. The arm assembly may include a wrist connector portion, a first integrated motor, and a second integrated motor. The arm assembly may be attachable to and detachable from the wrist assembly via the wrist connector portion. When the arm assembly is attached to the wrist assembly, the first instrument driven gear and the wrist driven gear are drivable to rotate by the first integrated motor and second integrated motor, respectively. When the wrist connector portion is detached from the wrist assembly, the first instrument driven gear and the wrist driven gear are not drivable to rotate by the first integrated motor and second integrated motor, respectively.

In another exemplary embodiment, a surgical arm assembly is disclosed. The surgical arm assembly may include an end-effector assembly and an arm assembly. The end-effector assembly may include an instrument assembly. The instrument assembly may include a first instrument having a proximal end and a distal end. The instrument assembly may also include a second instrument having a proximal end and a distal end. The instrument assembly may also include a first instrument driven portion. The first instrument driven portion may be configured in such a way as to drive the first instrument to rotate relative to a first central axis. The instrument assembly may also include a second instrument driven portion. The second instrument driven portion may be configured in such a way as to drive the second instrument to rotate relative to the first central axis. The arm assembly may include a connector portion, a first integrated motor, and a second integrated motor. The arm assembly may be attachable to and detachable from the end-effector assembly via the connector portion. When the arm assembly is attached to the end-effector assembly, the first instrument driven portion may be drivable by the first integrated motor to drive the first instrument to rotate relative to the first central axis. When the arm assembly is attached to the end-effector assembly, the second instrument driven portion may be drivable by the second integrated motor to drive the second instrument to rotate relative to the first central axis.

In another exemplary embodiment, a surgical arm assembly is disclosed. The surgical arm assembly may include an end-effector assembly and an arm assembly. The end-effector assembly may include a first instrument assembly and a wrist assembly. The first instrument assembly may include a first instrument having a proximal end and a distal end. The first instrument may be configurable to rotate relative to a first central axis. The wrist assembly may be connected to the first instrument assembly. The wrist assembly may include a wrist driven gear and a wrist body. The wrist body may connect the wrist driven gear to the first instrument assembly. When the wrist driven gear is driven to rotate, the first instrument assembly may be driven to rotate relative to a second central axis. The first central axis may be orthogonal to the second central axis. The first central axis may be non-coplanar to the first central axis. The arm assembly may include a wrist connector portion and a first integrated motor. The arm assembly may be attachable to and detachable from the wrist assembly via the wrist connector portion. When the arm assembly is attached to the wrist assembly, the wrist driven gear may be drivable to rotate by the first integrated motor. When the wrist connector portion is detached from the wrist assembly, the wrist driven gear may not be drivable to rotate by the first integrated motor.

In another exemplary embodiment, a surgical arm assembly is disclosed. The surgical arm assembly may be insertable into a cavity of a patient. The surgical arm assembly may be configurable for use in performing an in vivo surgical action. The surgical arm assembly may comprise an end-effector assembly. The end-effector assembly may comprise a first instrument assembly. The first instrument assembly may comprise a first instrument for performing a surgical action. The first instrument assembly may further comprise a first instrument driven portion configurable to be driven in such a way as to move the first instrument relative to a first axis. The first instrument assembly may further comprise a first instrument insulative portion providable between the first instrument and the first instrument driven portion. The first instrument insulative portion may be configurable to electrically isolate the first instrument from at least the first instrument driven portion when the first instrument insulative portion is provided between the first instrument and the first instrument driven portion.

In another exemplary embodiment, a surgical arm assembly is disclosed. The surgical arm assembly may be insertable into a cavity of a patient. The surgical arm assembly may be for use in performing an in vivo surgical action. The surgical arm assembly may comprise an end-effector assembly and an arm assembly. The end effector assembly may comprise a first instrument assembly. The first instrument assembly may comprise a first instrument for performing a surgical action. The first instrument assembly may further comprise a first instrument driven portion configurable to be driven in such a way as to move the first instrument relative to a first axis. The wrist assembly may be securable to the first instrument assembly. The wrist assembly may include a wrist driven portion configurable to be driven in such a way as to move the first instrument relative to a second axis, the second axis being different from the first axis. The arm assembly may be securable to and unsecurable from the wrist assembly. The arm assembly may comprise a wrist connector portion configurable to secure to and unsecure from the wrist assembly. The arm assembly may further comprise a first instrument drive portion secured to the wrist connector portion. The first instrument drive portion may be configurable to perform the driving of the first instrument driven portion when the wrist connector portion is secured to the wrist assembly. The arm assembly may further comprise a wrist drive portion secured to the wrist connector portion.

In another exemplary embodiment, a surgical arm assembly is disclosed. The surgical arm assembly may be insertable into a cavity of a patient. The surgical arm assembly may be for use in performing an in vivo surgical action. The surgical arm assembly may comprise an end-effector assembly and an arm assembly. The end-effector assembly may comprise a first instrument assembly and a second instrument assembly. The first instrument assembly may include a first instrument for performing a surgical action. The first instrument assembly may further include a first instrument driven portion configurable to be driven in such a way as to move the first instrument relative to a first axis. The first instrument assembly may further include a first instrument insulative portion providable between the first instrument and the first instrument driven portion. The first instrument insulative portion may be configurable to electrically isolate the first instrument from at least the first instrument driven portion when the first instrument insulative portion is provided between the first instrument and the first instrument driven portion. The second instrument assembly may include a second instrument for performing a surgical action. The second instrument assembly may further include a second instrument driven portion configurable to be driven in such a way as to move the second instrument relative to the first axis. The second instrument assembly may further include a second instrument insulative portion providable between the second instrument and the second instrument driven portion. The second instrument insulative portion may be configurable to electrically isolate the second instrument from at least the second instrument driven portion when the second instrument insulative portion is provided between the second instrument and the second instrument driven portion. The arm assembly may be securable to and unsecurable from the end-effector assembly. The arm assembly may comprise a wrist connector portion configurable to secure to and unsecure from the end-effector assembly. The arm assembly may further comprise a first instrument drive portion secured to the wrist connector portion. The first instrument drive portion may be configurable to perform the driving of the first instrument driven portion when the wrist connector portion is secured to the end-effector assembly. The arm assembly may further comprise a second instrument drive portion secured to the wrist connector portion. The second instrument drive portion may be configurable to perform the driving of the second instrument driven portion when the wrist connector portion is secured to the end-effector assembly. The arm assembly may further comprise a wrist drive portion secured to the wrist connector portion. The wrist drive portion may be configurable to perform the driving of the end-effector assembly in such a way as to collectively move the first instrument and the second instrument relative to a second axis when the wrist connector portion is secured to the wrist assembly.

In another exemplary embodiment, a surgical system is disclosed. The surgical system may comprise an end-effector assembly, a user interface, and a controller. The end-effector assembly may comprise a first instrument assembly. The first instrument assembly may include a first instrument for performing a surgical action. The first instrument assembly may further include a first instrument driven portion configurable to be driven in such a way as to move the first instrument relative to a first axis. The user interface may be configurable to receive user interactions being actions to be performed by the surgical arm assembly. The controller may be or include a processor configurable to receive, from the user interface, user interaction information representative of user interactions performed on the user interface. The controller may be or include a process configurable to process the received user interaction information. The controller may be or include a process configurable to transmit, based on the processing, one or more commands to the surgical arm assembly. The one or more commands may include commanding the first instrument drive portion to drive the first instrument driven portion in such a way as to cause a movement of the first instrument in a first direction relative to the first axis. The controller may be configurable to detect a resistance in a movement of at least a part of the end-effector assembly and communicate a haptic feedback response to the user interface. The controller may be configurable to receive, from the user interface, user interactions performed on the user interface representative of commanding an energy source to apply an electric current to the first instrument to perform the actions of an electrosurgical instrument.

In another exemplary embodiment, a surgical system is described. The surgical system may include an end-effector assembly. The end-effector assembly may include first instrument assembly. The first instrument assembly may include a first instrument, a first instrument driven portion, and a first instrument insulative portion. The first instrument may be configurable to receive an electric current. The first instrument may be configurable to perform an electrosurgical action when an electric current is applied to the first instrument. The first instrument driven portion may be configurable to be driven in such a way as to move the first instrument relative to a first axis. The first instrument insulative portion may be providable between the first instrument and the first instrument driven portion. The first instrument insulative portion may be configurable to prevent at least the first instrument driven portion from receiving an electric current applied to the first instrument when the first instrument insulative portion is provided between the first instrument and the first instrument driven portion.

In another exemplary embodiment, a surgical system is described. The surgical system may include an end-effector assembly and an arm assembly. The end-effector assembly may include a first instrument assembly and second instrument assembly. The first instrument assembly may include a first instrument insulative portion and first instrument. The first instrument may include a first elongated distal end for performing a surgical action and a second proximal end. The second proximal end of the first instrument may include an opening. The first instrument may be configurable to receive an electric current. The first instrument may be configurable to perform an electrosurgical action when an electric current is applied to the first instrument. The first instrument insulative portion may be provided in the opening of the first instrument. The first instrument insulative portion may be configurable to move the first elongated distal end of the first instrument relative to a first axis when a first gear assembly drives the first instrument insulative portion to rotate around the first axis. The first axis may be an axis drawn through a center of the opening of the first instrument and a center of the first instrument insulative portion. The first instrument insulative portion may be configurable to prevent at least the first gear assembly from receiving an electric current applied to the first instrument. The second instrument assembly may include a second instrument and a second instrument insulative portion. The second instrument may include a first elongated distal end for performing a surgical action and a second proximal end. The second proximal end of the second instrument may include an opening. The second instrument may be configurable to receive an electric current. The second instrument may be configurable to perform an electrosurgical action when an electric current is applied to the second instrument. The second instrument insulative portion may be provided in the opening of the second instrument. The second instrument insulative portion may be configurable to move the first elongated distal end of the second instrument relative to the first axis when a second gear assembly drives the second instrument insulative portion to rotate around the first axis. The second instrument insulative portion may be configurable to prevent at least the second gear assembly from receiving an electric current applied to the second instrument. The arm assembly may be securable to and unsecurable from the end effector assembly.

In another exemplary embodiment, a surgical system is described. The surgical system may include an end-effector assembly. The end-effector assembly includes a first instrument assembly. The first instrument assembly includes a first instrument and first instrument insulative portion. The first instrument includes a first elongated distal end for performing a surgical action and a second proximal end. The second proximal end of the first instrument may include a first instrument contact portion. The first instrument may be configurable to receive an electric current. The first instrument may be configurable to perform an electrosurgical action when an electric current is applied to the first instrument. The first instrument insulative portion may include a first contact portion and second contact portion. The first contact portion of the first instrument insulative portion may be configured to mate with the first instrument contact portion. The second contact portion of the first instrument insulative portion may be configured to mate with a first gear assembly so as to enable the first gear assembly to drive, via the first and second contact portions, the first elongated distal end of the first instrument to rotate relative to a first axis. The first axis may be an axis drawn through a center of the first instrument contact portion and a center of the first instrument insulative portion. The first instrument insulative portion may be configured to prevent at least the first gear assembly from receiving an electric current applied to the first instrument.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and:

FIG. 3A is an illustration of a side view of an example embodiment of a surgical arm assembly;

FIG. 3B is an illustration of a cross-sectional view of an example embodiment of a surgical arm assembly;

FIG. 4A is an illustration of a side view of an example embodiment of a surgical arm assembly;

FIG. 4B is an illustration of a cross-sectional view of an example embodiment of a surgical arm assembly;

Although similar reference numbers may be used to refer to similar elements in the figures for convenience, it can be appreciated that each of the various example embodiments may be considered to be distinct variations.

Figure 1:
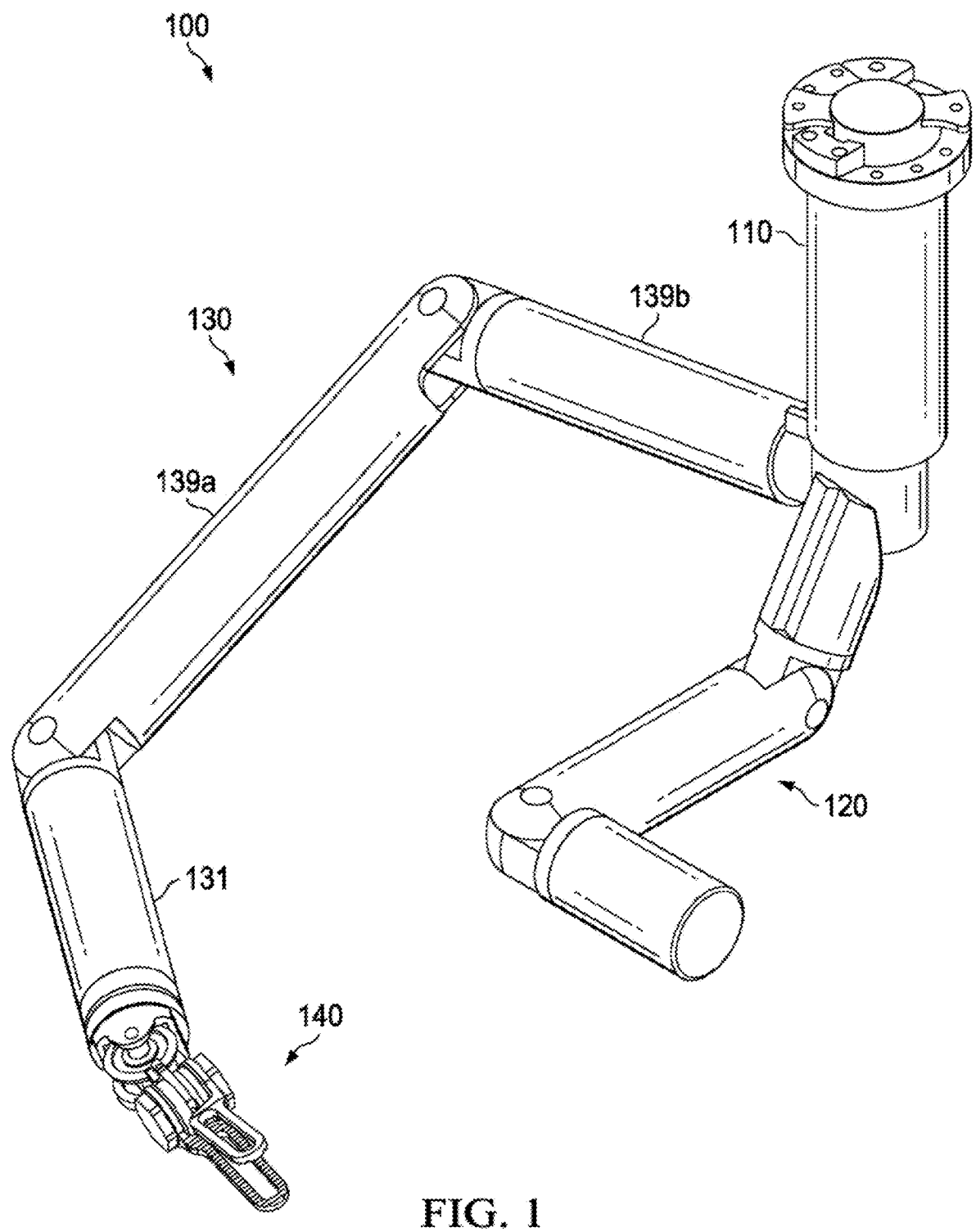
FIG. 1 is an illustration of a perspective view of an example embodiment of a surgical system.

Example embodiments will now be described with reference to the accompanying drawings, which form a part of the present disclosure, and which illustrate example embodiments which may be practiced. As used in the present disclosure and the appended claims, the terms "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an" and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

DETAILED DESCRIPTION

Despite recent developments in medical science and technology, problems continue to exist in modern surgical technology and methodology, including those pertaining to MIS and NOTES.

For example, a typical MIS procedure will generally require a surgeon to perform multiple incisions to a patient in order to enable the surgeon to insert, via such incisions, required laparoscopic instruments into the body cavity of the patient. Furthermore, it is recognized herein that a significant technical challenge encountered when using surgical robotic systems pertains to the difficulty in establishing sufficient anchoring and/or reactive forces to react to and/or stabilize against forces that need to be applied inside the body cavity of the patient by the surgical robotic system during a surgical action. In this regard, the use of known systems to perform certain surgical actions may require tremendous effort and time, and eventually may not be performed properly or at all due to such insufficient anchoring and/or reactive forces. Furthermore, surgeons using known surgical systems often encounter problems in respect to utilizing an instrument, such as a cutting and/or gripping instrument attached to the end of a surgical robotic arm, in certain parts, areas, and quadrants of a body cavity (such as an abdomen) of a patient after the system has been set up (or anchored) and ready to perform surgery. That is, after the surgical robotic arm of the system has been inserted and properly set up in the abdominal cavity of a patient, the surgical instrument attached to the end of the surgical robotic arm is typically mechanically limited to accessing only certain parts, areas, and quadrants of the abdominal cavity of the patient.

As another example, known surgical robotic systems typically only provide for between one to two surgical robotic arms per access or opening (such as an incision or a natural orifice) of the patient. In this regard, when additional laparoscopic instruments, such as another surgical robotic arm, a suction tube, and/or a camera, are required to be inserted into the abdominal cavity of the patient, one or more additional openings (incisions) are required to be performed on the patient. For such incisions, surgical teams also often encounter difficulties with properly inserting and removing surgical robotic systems, such as surgical robotic arms, into and out of the body cavity. Specifically, since surgical robotic arms generally have at least one joint and two arm segments, the insertion (and removal) of a surgical robotic arm into the body cavity oftentimes results in a portion of the surgical robotic arm (such as the end connected to an instrument, such as a cutting tool) coming into contact with and damaging patient tissue. This problem becomes compounded when a surgical procedure or system attempts to employ more than one surgical robotic arm through a single port.

Known surgical robotic systems also oftentimes face problems in respect to the heating up of one or more components during a surgical action, such as the heating up of laparoscopic optics (such as a camera), lighting elements, and other components. It is recognized in the present disclosure that increased temperature of such components may impose in-surgery and/or post-surgery damage or complications to patient tissues that come into contact with such components. Laparoscopic optics (such as a lens of a camera) and/or lighting elements in known surgical systems also tend to encounter contamination and/or partial or complete blockage during a surgical procedure due to fogging, tissue debris, liquids (such as blood), and/or other particles accumulated before, during, and/or after insertion of such components into the body cavity. In this regard, visibility within a body cavity via such laparoscopic optics and lighting elements may become reduced, deteriorated, or even completely blocked as a result.

Recent technological developments have introduced solutions to the aforementioned problems. U.S. patent application Ser. No. 14/693,207 to Yeung et al. ("US '207"), herein incorporated by reference in its entirety, describes surgical robotic devices, systems, and methods for solving the above-mentioned problems. For example, US '207 teaches a surgical system having a port assembly for use in providing sufficient anchoring and reactive forces to counter forces applied by a surgical arm of the surgical system during a surgical action. The surgical system of US '207 enables a surgeon to not only perform a single small incision to the patient but also enable the surgeon to utilize one or a plurality of laparoscopic instruments, including surgical robotic arms, suction tubes, and/or camera arms, in an abdominal cavity of the patient through such single small incision (via the port assembly). US '207 further teaches a surgical arm configurable to provide for 7 in vivo degrees of freedom, thereby enabling a surgical instrument attached to the surgical arm to access all parts, areas, and quadrants of a body cavity. The combined design of the port assembly, surgical robotic arms, and attachment portions for attaching the surgical robotic arms to the port assembly further enable easy and controllable insertion and removal of surgical robotic arms so as to prevent unintended contact with and damaging patient tissue.

In addition to the above-mentioned problems of known surgical systems encountered during forward-directed surgical procedures (e.g., MIS performed in an abdominal cavity of a patient), known surgical system generally encounter additional problems when deployed through a natural orifice, such as a rectum or vagina, for performing natural orifice transluminal endoscopic surgery (or NOTES), such as trans-vaginal gynecological procedures in women and trans-rectal urological procedures in men. For example, such known systems generally encounter problems pertaining to, among other things, the inability to access certain organs, tissues, or other surgical sites upon insertion into the natural orifice due as a result of the inherent forward-directed design of such systems.

Recent technological developments have introduced solutions to the aforementioned problems. For example, U.S. patent application Ser. No. 15/044,889 to Yeung ("US '889") and U.S. patent application Ser. No. 15/044,895 to Yeung ("US '895"), both herein incorporated by reference in their entireties, describe a surgical system configurable for use in performing forward-directed and/or reverse-directed surgical actions.

Surgical systems, devices, and methods, including those for use in MIS and NOTES, are described in the present disclosure. It is to be understood in the present disclosure that the principles described herein can be applied outside of the context of MIS and/or NOTES, such as performing scientific experiments and/or procedures in environments that are not readily accessible by humans, including in a vacuum, in outer space, and/or under toxic and/or dangerous conditions, without departing from the teachings of the present disclosure.

The Surgical System (e.g., Surgical System 100, 200)

FIG. 1 illustrates an example embodiment of a surgical device or surgical system (e.g., surgical device or surgical system 100) configurable for use in performing, among other things, a forward-directed surgical procedure. The surgical system 100 may be configurable to be inserted into an abdominal cavity of a patient via a single access or opening (e.g., a single incision (such as an incision in or around the umbilical area) or via a natural orifice (such as a rectum or vagina, for performing natural orifice transluminal endoscopic surgery (or NOTES), hereinafter referred to as an "opening") of the patient. The surgical system 100 may be anchored so as to position the surgical system 100 in the opening (e.g., a single incision) of the patient. The surgical system 100 may comprise a port assembly 110 and surgical arm assembly 130. The surgical system 100 may also comprise other laparoscopic elements, including, but not limited to, one or more other surgical arm assemblies, one or more image capturing assemblies, one or more assistant arm assemblies, one or more suction tubes, etc. Although FIG. 1 illustrates surgical system 100 having one surgical arm assembly 130 and one camera arm assembly 120, it is to be understood in the present disclosure that example embodiments may include one or more laparoscopic instruments including, but not limited to, one or more surgical arm assemblies, one or more camera arm assemblies, one or more assistant arm assemblies, and/or one or more suction tubes without departing from the teachings of the present disclosure.

Figure 2:
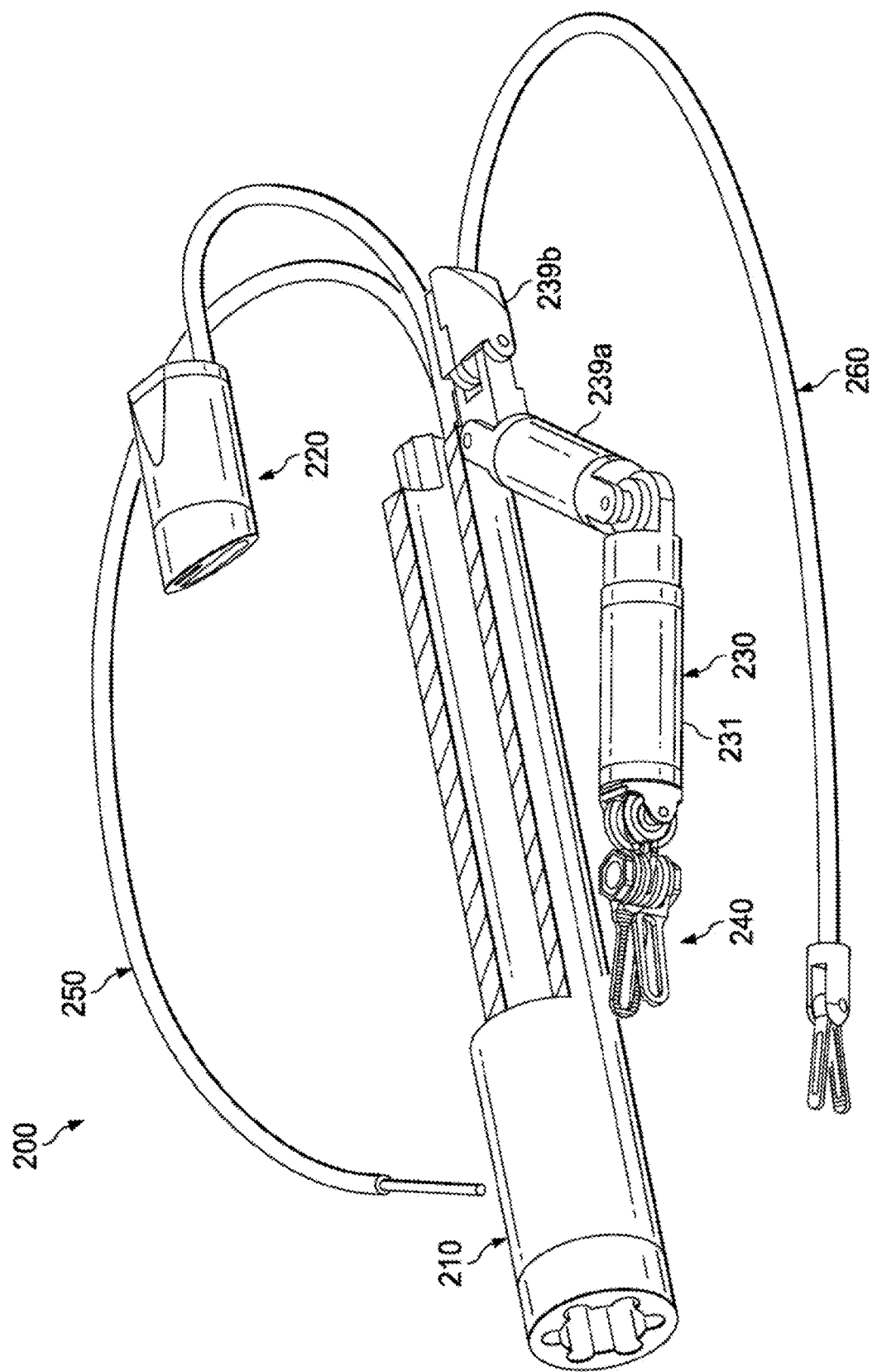
FIG. 2 is an illustration of a perspective view of another example embodiment of a surgical system.
Figure 5:
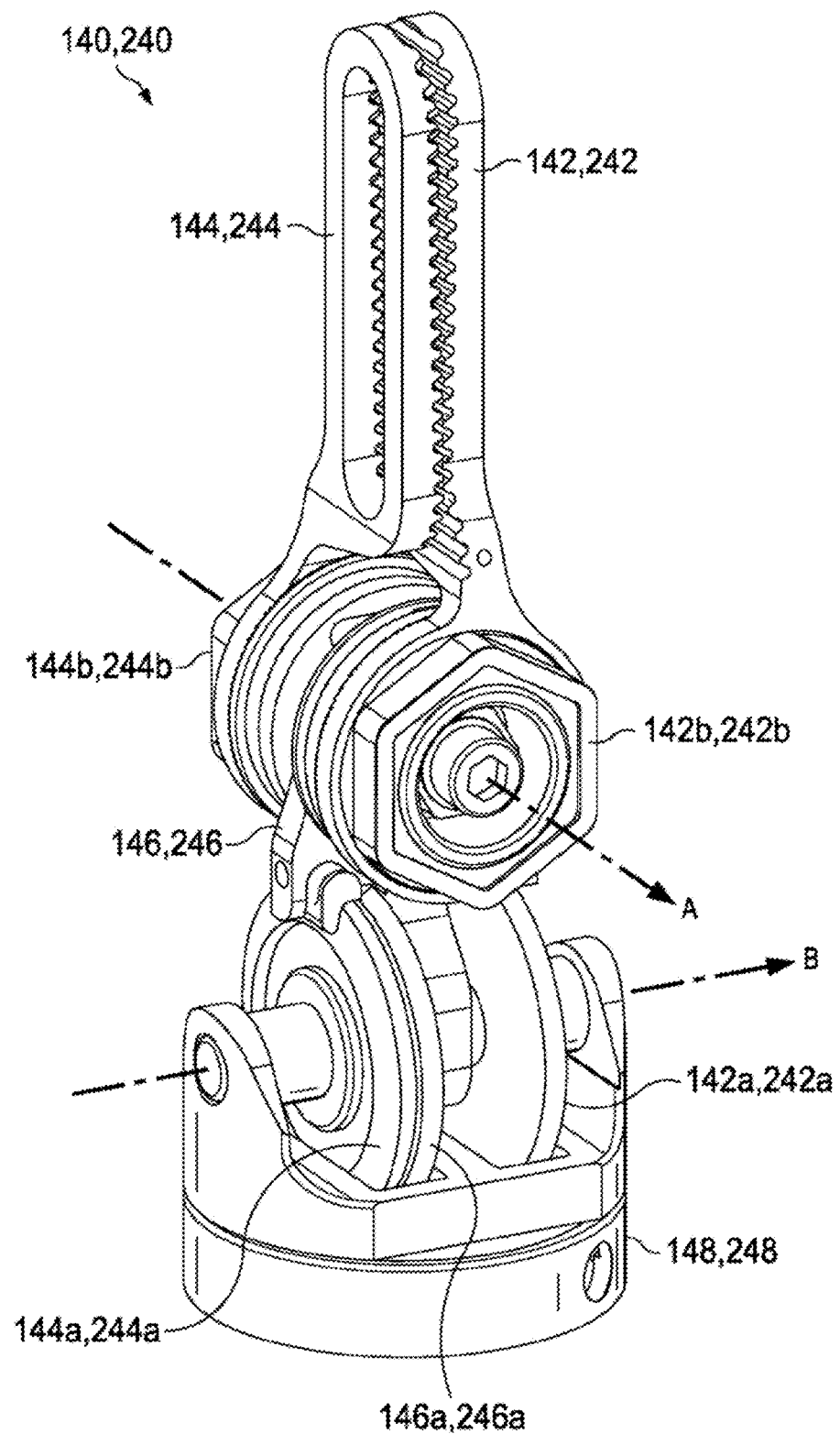
FIG. 5 is an illustration of a perspective view of an example embodiment of an end-effector assembly.
Figure 6:
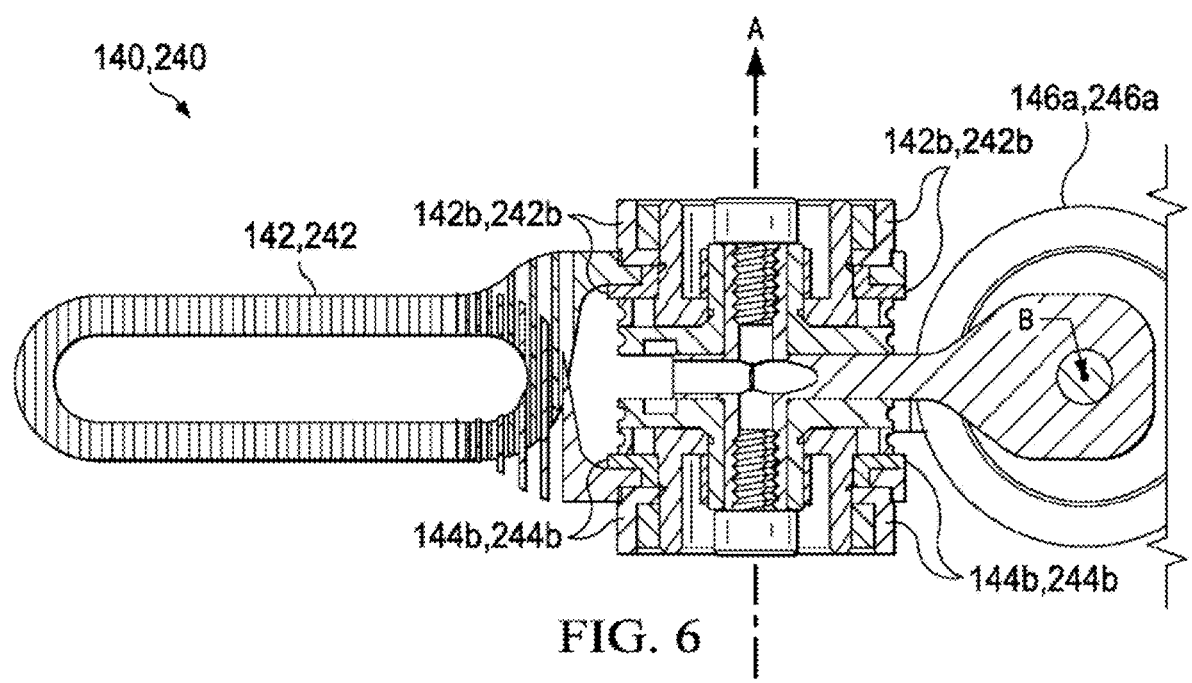
FIG. 6 is an illustration of a cross-sectional view of an example embodiment of an end-effector assembly.
Figure 7:
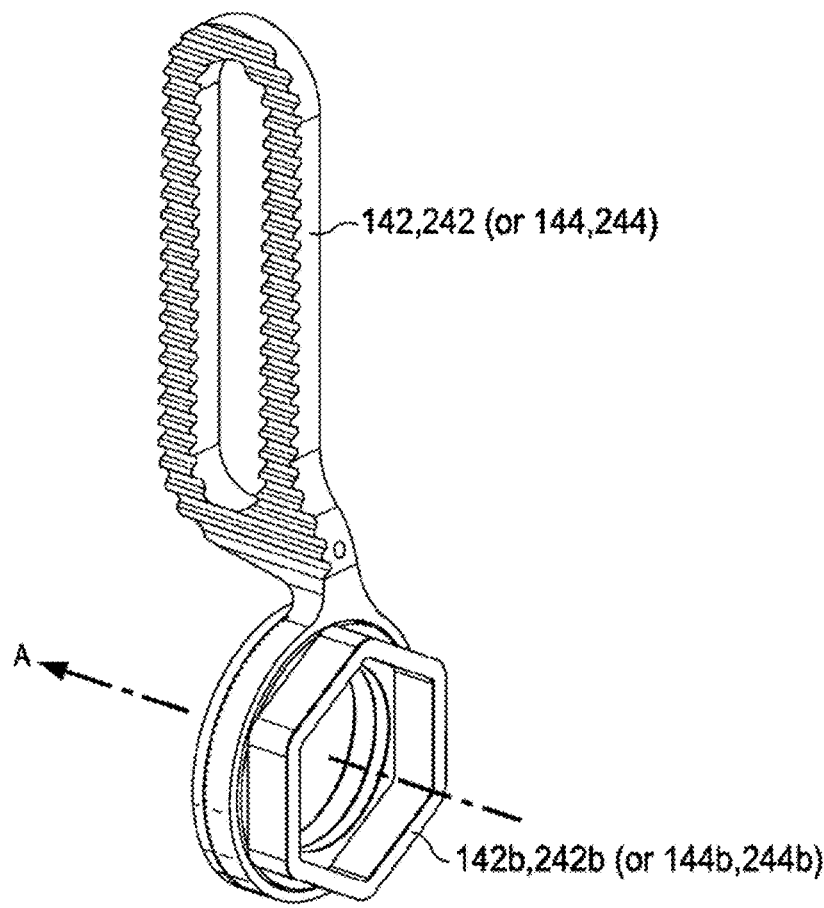
FIG. 7 is an illustration of a perspective view of an example embodiment of a first or second instrument and a first or second instrument insulative portion.

FIG. 2 illustrates an example embodiment of another surgical device or surgical system (e.g., surgical device or surgical system 200) configurable for use in performing, among other things, a reverse-directed surgical procedure. The surgical system 200 may be configurable to be inserted into an opening of a patient. Although FIG. 1 illustrates one surgical arm assembly and one camera arm assembly, it is to be understood in the present disclosure that example embodiments may include (or not include) one or more laparoscopic instruments, including one or more surgical arm assemblies, one or more camera arm assemblies, one or more assistant arm assemblies, and/or one or more suction tubes. The surgical system 200 may be anchored so as to position the surgical system 200 in the opening (e.g., a natural orifice) of the patient. The surgical system 200 may comprise a port assembly 210 and surgical arm assembly 230. The surgical system 200 may also comprise other laparoscopic elements, including, but not limited to, one or more other surgical arm assemblies, one or more image capturing assemblies, one or more assistant arm assemblies (e.g., assistant arm assemblies 250, 260), one or more suction tubes, etc. Although FIG. 2 illustrates surgical system 200 having one surgical arm assembly 230, one camera arm assembly 220, and two assistant arm assemblies 250, 260, it is to be understood in the present disclosure that example embodiments may include one or more laparoscopic instruments including, but not limited to, one or more surgical arm assemblies, one or more camera arm assemblies, one or more assistant arm assemblies, and/or one or more suction tubes without departing from the teachings of the present disclosure.

The Surgical Arm Assembly (e.g., Surgical Arm Assembly 130)

In an example embodiment, the surgical device 100, 200 may comprise one or more surgical arm assemblies, including a first surgical arm assembly (e.g., the surgical arm assembly 130, 230), second surgical arm assembly (not shown), third surgical arm assembly (not shown), fourth surgical arm assembly (not shown), etc.). Each surgical arm assembly may be configurable to secure to and unsecure from the port assembly 210.

Figure 9A:
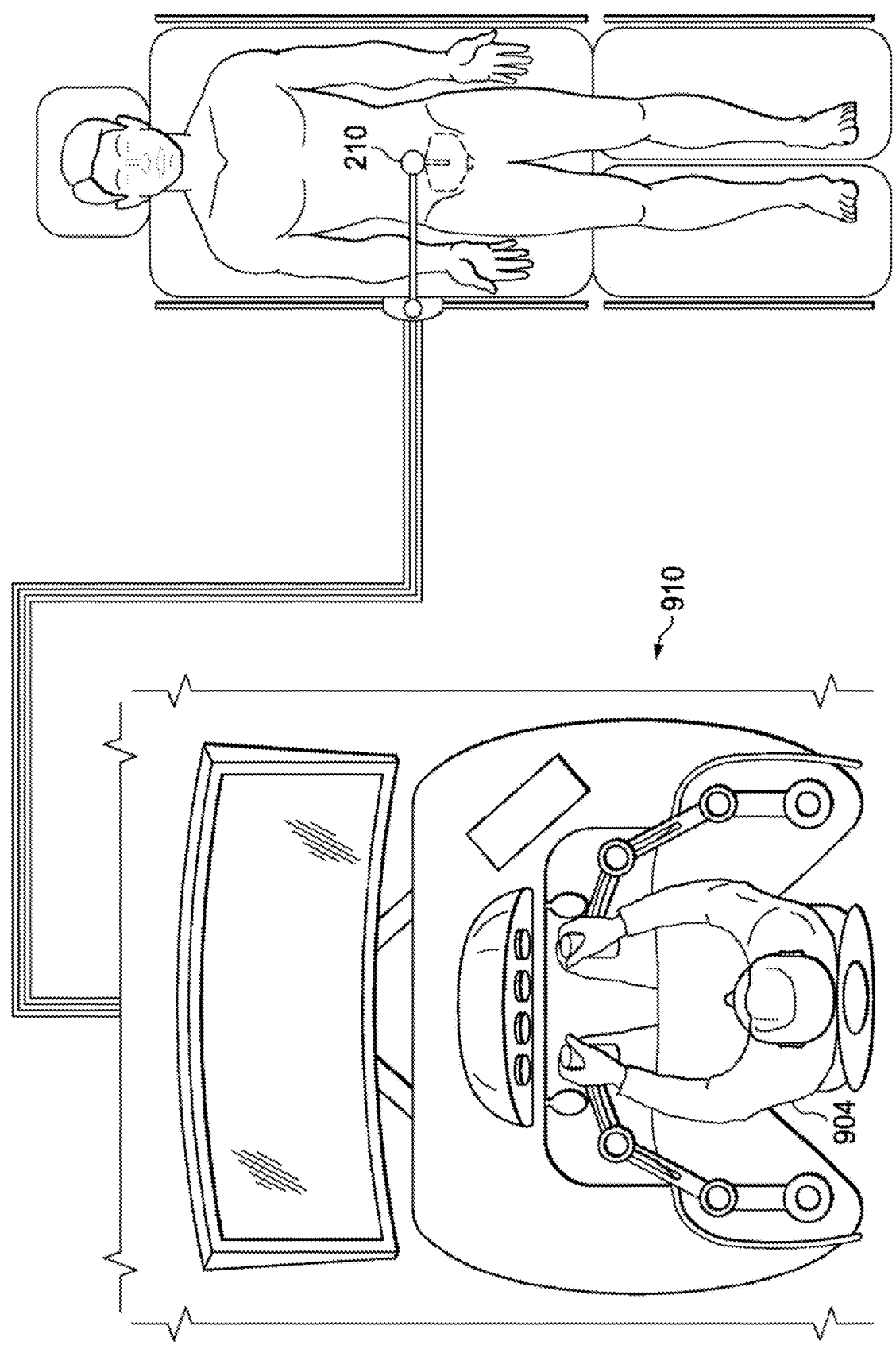
FIG. 9A is an illustration of a top view of an example embodiment of a surgical system.
Figure 9B:
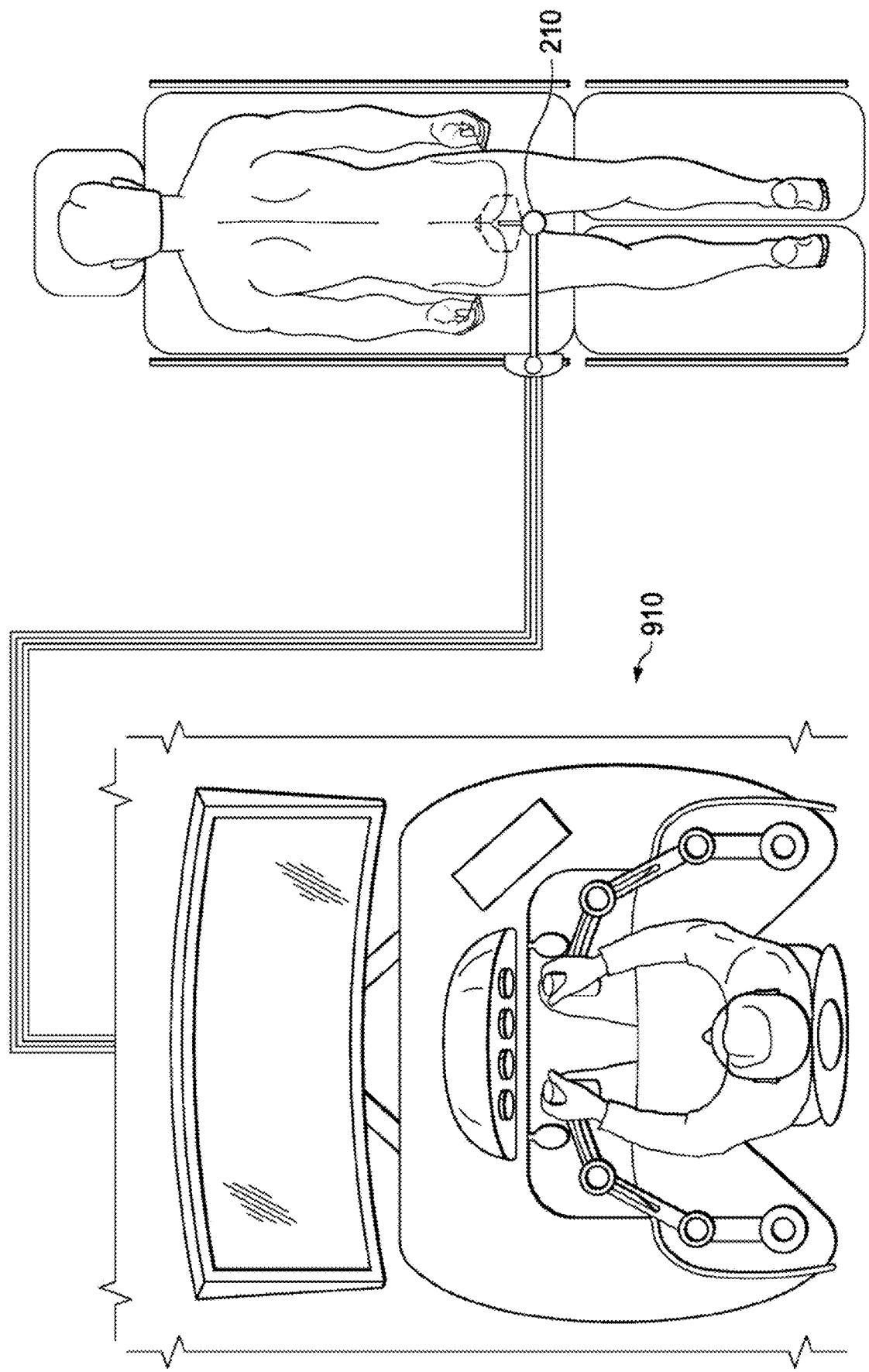
FIG. 9B is an illustration of a top view of another example embodiment of a surgical system.

One or more of the surgical arm assemblies (e.g., surgical arm assembly 130, 230) may comprise a configurable serial (or linear) arrangement of a plurality of surgical arm segments, including arm assembly (e.g., arm assembly 131, 231), joint portions, and at least one end-effector assembly (e.g., end-effector assembly 140, 240). For example, as illustrated in FIG. 3A and FIG. 4A and cross-section views illustrated in FIG. 3B and FIG. 4B, a surgical arm assembly (e.g., surgical arm assembly 130, 230) may comprise an arm assembly (e.g., arm assembly 131, 231) and an end-effector assembly (e.g., end-effector assembly 140, 240). One or more of the surgical arm assemblies (e.g., surgical arm assembly 130, 230) may include integrated haptic and/or force feedback subsystems (not shown) configurable to provide to a haptic feedback response to a user interface (e.g., a user interface for use by a surgeon or assistant), and such haptic feedback response may be first processed by a controller (not shown). An example embodiment of such user interface (e.g., user interface 910) is illustrated in FIG. 9A and FIG. 9B. The one or more surgical arm assemblies (e.g., surgical arm assembly 130, 230) may also be configurable to provide the controller and/or user interface (e.g., user interface 910) with one or more of a plurality of feedback responses and/or measurements, including those pertaining to position (including orientation), applied force, proximity, temperature, pressure, humidity, etc., of, by, and/or nearby to the surgical arm assembly (e.g., surgical arm assembly 130, 230). In addition to the haptic feedback response, the controller may be further configurable to, among other things, translate, replicate, map, and/or sense the delicate movements of the operator using the user interface (e.g., user interface 910) into movements of the surgical arm assembly (e.g., surgical arm assembly 130, 230) with high precision, high dexterity, and minimum burden.

One or more of the surgical arm assemblies (e.g., surgical arm assembly 130, 230) may also be configurable to receive an electric current (or voltage potential, thermal energy, heat, cold temperature application, etc.) from an energy source (or other source, not shown). In example embodiments, such an energy source (or other source) may also be integrated, in part or in whole, into one or more of the surgical arm assemblies (e.g., surgical arm assembly 130, 230). The electrical current (or voltage potential, thermal energy, heat, or cold temperature application) from the energy source (or other source) may be selectively applied to one or more elements of the end-effector assembly (e.g., end-effector assembly 140, 240), and such selective application of the electric current (or voltage potential, thermal energy, heat, cold temperature application, etc.) may be configured and/or controlled by the user interface (e.g., via the controller). For example, in situations wherein the end-effector assembly (e.g., end-effector assembly 140, 240) includes a first instrument (e.g., first instrument 142, 242) and a second instrument (e.g., second instrument 144, 244), an operator of the user interface (e.g., user interface 910) may configure the user interface (e.g., user interface 910) to command (e.g., via the controller) the energy source (or other source) to apply the electric current (or voltage potential, thermal energy, heat, cold temperature application, etc.) to the first instrument (e.g., first instrument 142, 242). It is recognized in the present disclosure that the application of such electric current (or voltage potential, thermal energy, heat, cold temperature application, etc.) to the first instrument (e.g., first instrument 142, 242) alone or in collective operation with second instrument (e.g., second instrument 144, 244) enables the end-effector assembly (e.g., end-effector assembly 140, 240) to perform the actions of an electrosurgical instrument, or the like.

These and other elements and example embodiments of the surgical system and surgical arm assembly (e.g., surgical arm assembly 130, 230) will now be further described with reference to the accompanying figures.

Example Embodiment of a Surgical Arm Assembly

As illustrated in FIGS. 3A-B and 4A-B, an example embodiment of a surgical arm assembly (e.g., surgical arm assembly 130, 230) may comprise an arm assembly (e.g., arm assembly 131, 231) and an end-effector assembly (e.g., end-effector assembly 140, 240).

Arm Assembly (e.g., Arm Assembly 131, 231)

In an example embodiment, the arm assembly (e.g., arm assembly 131, 231) may be secured via a joint to another part of the surgical arm assembly (e.g., arm section 139*a*, 239*a*), as illustrated in FIGS. 1 and 2. Such other part of the surgical arm assembly (e.g., arm section 139*a*, 239*a*) may itself be connected to another part of the surgical arm assembly (e.g., shoulder section 139*b*, 239*b*), which may inturn be connected to the port assembly (e.g., port assembly 110, 210).

The arm assembly (e.g., arm assembly 131, 231) may include a first instrument drive portion (e.g., first instrument drive portion 132, 232). The arm assembly (e.g., arm assembly 132, 232) may further include a second instrument drive portion (e.g., second instrument drive portion 134, 234). Although the figures illustrate an arm assembly having a first instrument drive portion and a second instrument drive portion, it is to be understood in the present disclosure that the arm assembly may have more other instrument drive portions or may only have a first instrument drive portion or a second instrument drive portion without departing from the teachings of the present disclosure. The arm assembly (e.g., arm assembly 131, 231) may also include a wrist drive portion (e.g., wrist drive portion 136, 236). The arm assembly (e.g., arm assembly 131, 231) may further include a wrist connector portion (e.g., wrist connector portion 138, 238).

(i) First Instrument Drive Portion (e.g., First Instrument Drive Portion 131, 231)

The first instrument drive portion (e.g., first instrument drive portion 132, 232) may be any mechanism, device, or the like, configurable to drive (e.g., cause a movement of) the first instrument driven portion (e.g., first instrument driven portion 142*a*, 242*a*, as further described below and in the present disclosure) of the end-effector assembly (e.g., end-effector assembly 140, 240). For example, the first instrument drive portion (e.g., first instrument drive portion 132, 232) may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one first instrument drive portion, it is to be understood in the present disclosure that the arm assembly may have more than one first instrument drive portions (e.g., when the end-effector assembly includes more than one first instrument driven portions) without departing from the teachings of the present disclosure.

(ii) Second Instrument Drive Portion (e.g., First Instrument Drive Portion 134, 234)

The second instrument drive portion (e.g., second instrument drive portion 134, 234) may be any mechanism, device, or the like, configurable to drive (e.g., cause a movement of) the second instrument driven portion (e.g., second instrument driven portion 144*a*, 244*a*, as further described below and in the present disclosure). For example, the second instrument drive portion (e.g., second instrument drive portion 134, 234) may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one second instrument drive portion, it is to be understood in the present disclosure that the arm assembly may have more than one second instrument drive portions (e.g., when the end-effector assembly includes more than one second instrument driven portions) without departing from the teachings of the present disclosure.

(iii) Wrist Drive Portion (e.g., Wrist Drive Portion 136, 236)

The wrist drive portion (e.g., wrist drive portion 136, 236) may be any mechanism, device, or the like, configurable to drive (e.g., cause a movement of) the wrist driven portion (e.g., wrist driven portion 146a, 246a, as further described below and in the present disclosure). For example, the wrist drive portion (e.g., wrist drive portion 136, 236) may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one wrist drive portion, it is to be understood in the present disclosure that the arm assembly may have more than one wrist drive portions without departing from the teachings of the present disclosure.

In an example embodiment, the first instrument drive portion (e.g., first instrument drive portion 132, 232) and the second instrument drive portion (e.g., second instrument drive portion 134, 234) may be selectively driven independently from one another. In example embodiments, the first instrument drive portion (e.g., first instrument drive portion 132, 232) and the second instrument drive portion (e.g., second instrument drive portion 134, 234) may be selectively driven in a similar or same manner, such as being driven at the same time, for the same duration, and/or with the same output energy, torque, and/or rotations per minute (rpm).

The wrist connector portion (e.g., wrist connector portion 138, 238) may be any connector portion for use in securing to and unsecuring from the wrist assembly (the wrist assembly comprising a wrist driven portion (e.g., wrist driven portion 146a, 146b), as further described below and in the present disclosure). Put differently, the wrist connector portion (e.g., wrist connector portion 138, 238) is configurable to secure and unsecure the arm assembly (e.g., arm assembly 131, 231) to and from the end-effector assembly (e.g., end-effector assembly 140, 240), respectively. Accordingly, the end-effector assembly (e.g., end-effector assembly 140, 240) may be detached/unsecured from the arm assembly (e.g., arm assembly 131, 231) when not needed and attached/secured to the arm assembly (e.g., arm assembly 131, 231) when needed to perform a surgical action.

End-Effector Assembly (e.g., End-Effector Assembly 140, 240)

As illustrated in at least FIGS. 3-8, an example embodiment of the end-effector assembly (e.g., end-effector assembly 140, 240) may comprise a first instrument assembly. The end-effector assembly (e.g., end-effector assembly 140, 240) may also comprise a second instrument assembly. Although the figures illustrate an end-effector assembly having a first instrument and a second instrument, it is to be understood in the present disclosure that the end-effector assembly may have more other instruments or may only have a first instrument or a second instrument without departing from the teachings of the present disclosure. The end-effector assembly (e.g., end-effector assembly 140, 240) may also comprise wrist assembly.

(i) First Instrument Assembly

An example embodiment of the first instrument assembly may comprise a first instrument (e.g., first instrument 142, 242) for use in performing a surgical action. The first instrument (e.g., first instrument 142, 242) may be any surgical instrument without departing from the teachings of the present disclosure.

In an example embodiment, the first instrument (e.g., first instrument 142, 242) may be configurable to receive an electric current (e.g., first electric current) applied from a first energy source (not shown) so as to perform actions of an electrosurgical instrument. Although the first instrument may be described above and in the present disclosure to receive an electric current, it is to be understood that the first instrument may also be configurable to receive a voltage potential, thermal energy, heat, cold temperature application, radiation, etc. to perform the said surgical action without departing from the teachings of the present disclosure.

The first instrument assembly may comprise a first instrument driven portion (e.g., first instrument driven portion 142a, 242a). The first instrument driven portion (e.g., first instrument driven portion 142a, 242a) may be configurable to be driven by the first instrument drive portion (e.g., first instrument drive portion 132, 232) of the arm assembly (e.g., arm assembly 131, 231). The first instrument driven portion (e.g., first instrument driven portion 142a, 242a) may be driven by the first instrument drive portion (e.g., first instrument drive portion 132, 232) in such a way as to move the first instrument (e.g., first instrument 142, 242). For example, the first instrument driven portion (e.g., first instrument driven portion 142a, 242a) may be driven to move the first instrument (e.g., first instrument 142, 242) relative to a first axis (e.g., axis A, as illustrated in FIGS. 4-8). In this regard, such movement of the first instrument (e.g., first instrument 142, 242) may be a rotation of a distal end of the first instrument (e.g., first instrument 142, 242) relative to a proximal end of the first instrument (e.g., first instrument 142, 242), and such proximal end may serve as a pivot for such movement.

The first instrument driven portion (e.g., first instrument driven portion 142a, 242a) may be any mechanism, device, or the like, configurable to be driven by the first instrument drive portion (e.g., first instrument drive portion 132, 232). For example, the first instrument driven portion (e.g., first instrument driven portion 142a, 242a) may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one first instrument driven portion, it is to be understood in the present disclosure that the end-effector assembly may have more than one first instrument driven portions without departing from the teachings of the present disclosure.

In example embodiments wherein the end-effector assembly (e.g., end-effector assembly 140, 240) is detachable (i.e., unsecurable) from the arm assembly (e.g., arm assembly 131, 231), it is to be understood that the first instrument drive portion (e.g., first instrument drive portion 132, 232) of the arm assembly (e.g., arm assembly 131, 231) may be operable to drive the first instrument driven portion (e.g., first instrument driven portion 142a, 242a) when the end-effector assembly (e.g., end-effector assembly 140, 240) is secured (i.e., attached) to the arm assembly (e.g., arm assembly 131, 231). Specifically, the first instrument drive portion (e.g., first instrument drive portion 132, 232) of the arm assembly (e.g., arm assembly 131, 231) may be operable to drive the first instrument driven portion (e.g., first instrument driven portion 142a, 242a) when the wrist connector portion (e.g., wrist connector portion 136, 236) is secured (i.e., attached) to the wrist assembly (as further described below and in the present disclosure) of the end-effector assembly (and more specifically, the connector (e.g., connector 148, 248) of the end-effector assembly (e.g., end-effector assembly 140, 240)).

In example embodiments wherein the end-effector assembly (e.g., end-effector assembly 140, 240) is detachable (i.e., unsecurable) from the arm assembly (e.g., arm assembly 131, 231), it is to be understood that one or more connectable and unconnectable electric wires, cables, or the like, may be provided to enable the first instrument (e.g., first instrument 142, 242) to receive the electric current from the energy source to perform the actions of an electrosurgical instrument.

The first instrument assembly may comprise a first instrument insulative portion (e.g., first instrument insulative portion 142b, 242b). The first instrument insulative portion (e.g., first instrument insulative portion 142b, 242b) may be providable between the first instrument (e.g., first instrument 142, 242) and one or more portions of the end-effector assembly (e.g., end-effector assembly 140, 240) so as to electrically isolate (or electrically insulate, thermally isolate, thermally insulate, and the like) the first instrument (e.g., first instrument 142, 242) from the one or more portions of the end-effector assembly (e.g., end-effector assembly 140, 240). In an example embodiment, the first instrument insulative portion (e.g., first instrument insulative portion 142b, 242b) may be providable between the first instrument (e.g., first instrument 142, 242) and the first instrument driven portion (e.g., first instrument driven portion 142a, 242a) so as to electrically isolate (or electrically insulate, thermally isolate, thermally insulate, and the like) the first instrument (e.g., first instrument 142, 242) from the first instrument driven portion (e.g., first instrument driven portion 142a, 242a). Such electric isolation (or electric insulation, thermal isolation, thermal insulation, and the like) may be desirable to protect electrically (or thermally) sensitive components/portions of the surgical arm assembly and/or also prevent such electric current (or voltage potential, thermal energy, heat, cold temperature application, radiation, etc.) from undesirably passing through to the second instrument (e.g., second instrument 144, 244) via the first instrument driven portion (e.g., first instrument driven portion 142a, 242a) and/or other component/portion of the surgical arm assembly.

The first instrument insulative portion (e.g., first instrument insulative portion 142b, 242b) may be formed using any one or more of a plurality of materials, such as electrically insulative materials, thermally insulative materials, plastics, elastomers, ceramics, glasses and minerals. It is to be understood in the present disclosure that other materials may also be used without departing from the teachings of the present disclosure.

The first instrument (e.g., first instrument 142, 242) may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), cobalt-chromium alloys, and magnesium alloys. It is to be understood in the present disclosure that other materials may also be used without departing from the teachings of the present disclosure. Furthermore, the first instrument (e.g., first instrument 142, 242) may include an opening, or the like, for use in receiving and housing at least a portion of the first instrument insulative portion (e.g., first instrument insulative portion 142b, 242b). The first axis (e.g., axis A) may be formed through a center of the opening of the first instrument (e.g., first instrument 142, 242) in example embodiments. Although the opening may be depicted in the figures to be circular in shape and the corresponding exterior portion of the first instrument insulative portion (e.g., first instrument insulative portion 142b, 242b) being housed in the opening may be depicted in the figures to be circular in shape, it is to be understood in the present disclosure that the opening and such corresponding exterior portion may be formed in one or more other shapes, including, but not limited to, a square, rectangle, oval, pentagon, hexagon, etc., without departing from the teachings of the present disclosure.

(ii) Second Instrument Assembly

An example embodiment of the second instrument assembly may comprise a second instrument (e.g., second instrument 144, 244) for use in performing a surgical action. The second instrument (e.g., second instrument 144, 244) may be any surgical instrument without departing from the teachings of the present disclosure.

In an example embodiment, the second instrument (e.g., second instrument 144, 244) may be configurable to receive an electric current (e.g., second electric current) applied from a second energy source (not shown) so as to perform actions of an electrosurgical instrument. Although the second instrument may be described above and in the present disclosure to receive an electric current, it is to be understood that the second instrument may also be configurable to receive a voltage potential, thermal energy, heat, cold temperature application, radiation, etc. to perform the said surgical action without departing from the teachings of the present disclosure.

The second instrument assembly may comprise a second instrument driven portion (e.g., second instrument driven portion 144a, 244a). The second instrument driven portion (e.g., second instrument driven portion 144a, 244a) may be configurable to be driven by the second instrument drive portion (e.g., second instrument drive portion 134, 234) of the arm assembly (e.g., arm assembly 131, 231). The second instrument driven portion (e.g., second instrument driven portion 144a, 244a) may be driven by the second instrument drive portion (e.g., second instrument drive portion 134 234) in such a way as to move the second instrument (e.g., second instrument 144, 244). For example, the second instrument driven portion (e.g., second instrument driven portion 144a, 244a) may be driven to move the second instrument (e.g., second instrument 144, 244) relative to the first axis (e.g., axis A, as illustrated in FIGS. 4-8). In this regard, such movement of the second instrument (e.g., second instrument 144, 244) may be a rotation of a distal end of the second instrument (e.g., second instrument 144, 244) relative to a proximal end of the second instrument (e.g., second instrument 144, 244), and such proximal end may serve as a pivot for such movement.

The second instrument driven portion (e.g., second instrument driven portion 144a, 244a) may be any mechanism, device, or the like, configurable to be driven by the second instrument drive portion (e.g., second instrument drive portion 134, 234). For example, the second instrument driven portion (e.g., second instrument driven portion 144a, 244a) may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one second instrument driven portion, it is to be understood in the present disclosure that the end-effector assembly may have more than one second instrument driven portions without departing from the teachings of the present disclosure.

In example embodiments wherein the end-effector assembly (e.g., end-effector assembly 140, 240) is detachable (i.e., unsecurable) from the arm assembly (e.g., arm assembly 131, 231), it is to be understood that the second instrument drive portion (e.g., second instrument drive portion 134, 234) of the arm assembly (e.g., arm assembly 131, 231) may be operable to drive the second instrument driven portion (e.g., second instrument driven portion 144a, 244a) when the end-effector assembly (e.g., end-effector assembly 140, 240) is secured (i.e., attached) to the arm assembly (e.g., arm assembly 131, 231). Specifically, the second instrument drive portion (e.g., second instrument drive portion 134, 234) of the arm assembly (e.g., arm assembly 131, 231) may be operable to drive the second instrument driven portion (e.g., second instrument driven portion 144a, 244a) when the wrist connector portion (e.g., wrist connector portion 136, 236) is secured (i.e., attached) to the wrist assembly (as further described below and in the present disclosure) of the end-effector assembly (and more specifically, the connector (e.g., connector 148, 248) of the end-effector assembly (e.g., end-effector assembly 140, 240)).

In example embodiments wherein the end-effector assembly (e.g., end-effector assembly 140, 240) is detachable (i.e., unsecurable) from the arm assembly (e.g., arm assembly 131, 231), it is to be understood that one or more connectable and unconnectable electric wires, cables, or the like, may be provided to enable the second instrument (e.g., second instrument 144, 244) to receive the electric current from the energy source to perform the actions of an electrosurgical instrument.

The second instrument assembly may comprise a second instrument insulative portion (e.g., second instrument insulative portion 144b, 244b). The second instrument insulative portion (e.g., second instrument insulative portion 144b, 244b) may be providable between the second instrument (e.g., second instrument 144, 244) and one or more portions of the end-effector assembly (e.g., end-effector assembly 140, 240) so as to electrically isolate (or electrically insulate, thermally isolate, thermally insulate, and the like) the second instrument (e.g., second instrument 144, 244) from the one or more portions of the end-effector assembly (e.g., end-effector assembly 140, 240). In an example embodiment, the second instrument insulative portion (e.g., second instrument insulative portion 144b, 244b) may be providable between the second instrument (e.g., second instrument 144, 244) and the second instrument driven portion (e.g., second instrument driven portion 144a, 244a) so as to electrically isolate (or electrically insulate, thermally isolate, thermally insulate, and the like) the second instrument (e.g., second instrument 144, 244) from the second instrument driven portion (e.g., second instrument driven portion 144a, 244a). Such electric isolation (or electric insulation, thermal isolation, thermal insulation, and the like) may be desirable to protect electrically (or thermally) sensitive components/portions of the surgical arm assembly and/or also prevent such electric current (or voltage potential, thermal energy, heat, cold temperature application, radiation, etc.) from undesirably passing through to the first instrument (e.g., first instrument 142, 242) via the second instrument driven portion (e.g., second instrument driven portion 144a, 244a) and/or other component/portion of the surgical arm assembly.

The second instrument insulative portion (e.g., second instrument insulative portion 144b, 244b) may be formed using any one or more of a plurality of materials, such as electrically insulative materials, thermally insulative materials, plastics, elastomers, ceramics, glasses and minerals. It is to be understood in the present disclosure that other materials may also be used without departing from the teachings of the present disclosure.

The second instrument (e.g., second instrument 144, 244) may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), cobalt-chromium alloys, and magnesium alloys. It is to be understood in the present disclosure that other materials may also be used without departing from the teachings of the present disclosure. Furthermore, the second instrument (e.g., second instrument 144, 244) may include an opening, or the like, for use in receiving and housing at least a portion of the second instrument insulative portion (e.g., second instrument insulative portion 144b, 244b, as illustrated in at least FIGS. 5-8). The first axis (e.g., axis A) may be formed through a center of the opening of the second instrument (e.g., second instrument 144, 244) in example embodiments. Although the opening may be depicted in the figures to be circular in shape and the corresponding exterior portion of the second instrument insulative portion (e.g., second instrument insulative portion 144b, 244b) being housed in the opening may be depicted in the figures to be circular in shape, it is to be understood in the present disclosure that the opening and such corresponding exterior portion may be formed in one or more other shapes, including, but not limited to, a square, rectangle, oval, pentagon, hexagon, etc., without departing from the teachings of the present disclosure.

Figure 8A:
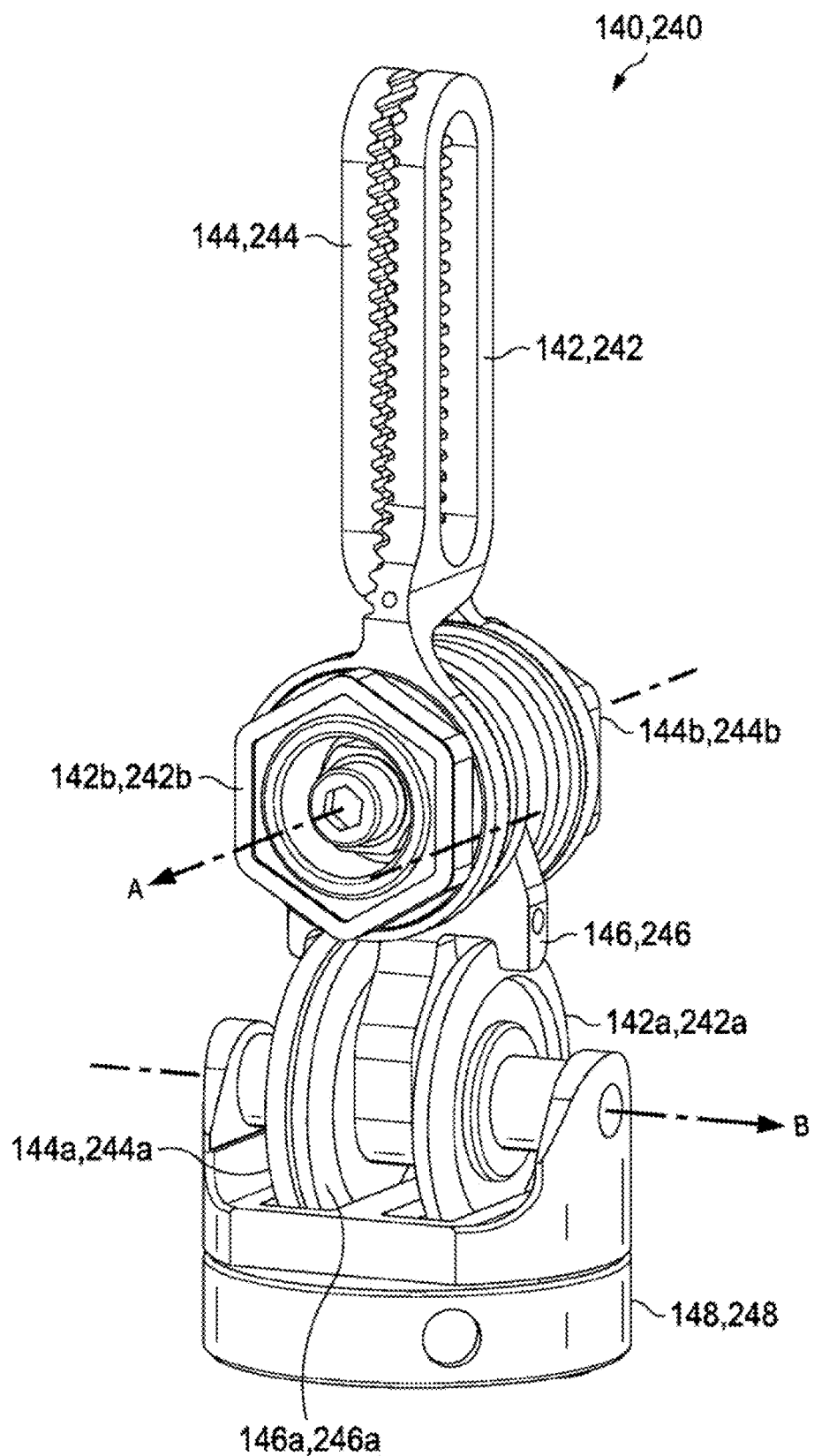
FIG. 8A is an illustration of a perspective view of an example embodiment of an end-effector assembly in the form of a grasper.
Figure 8B:
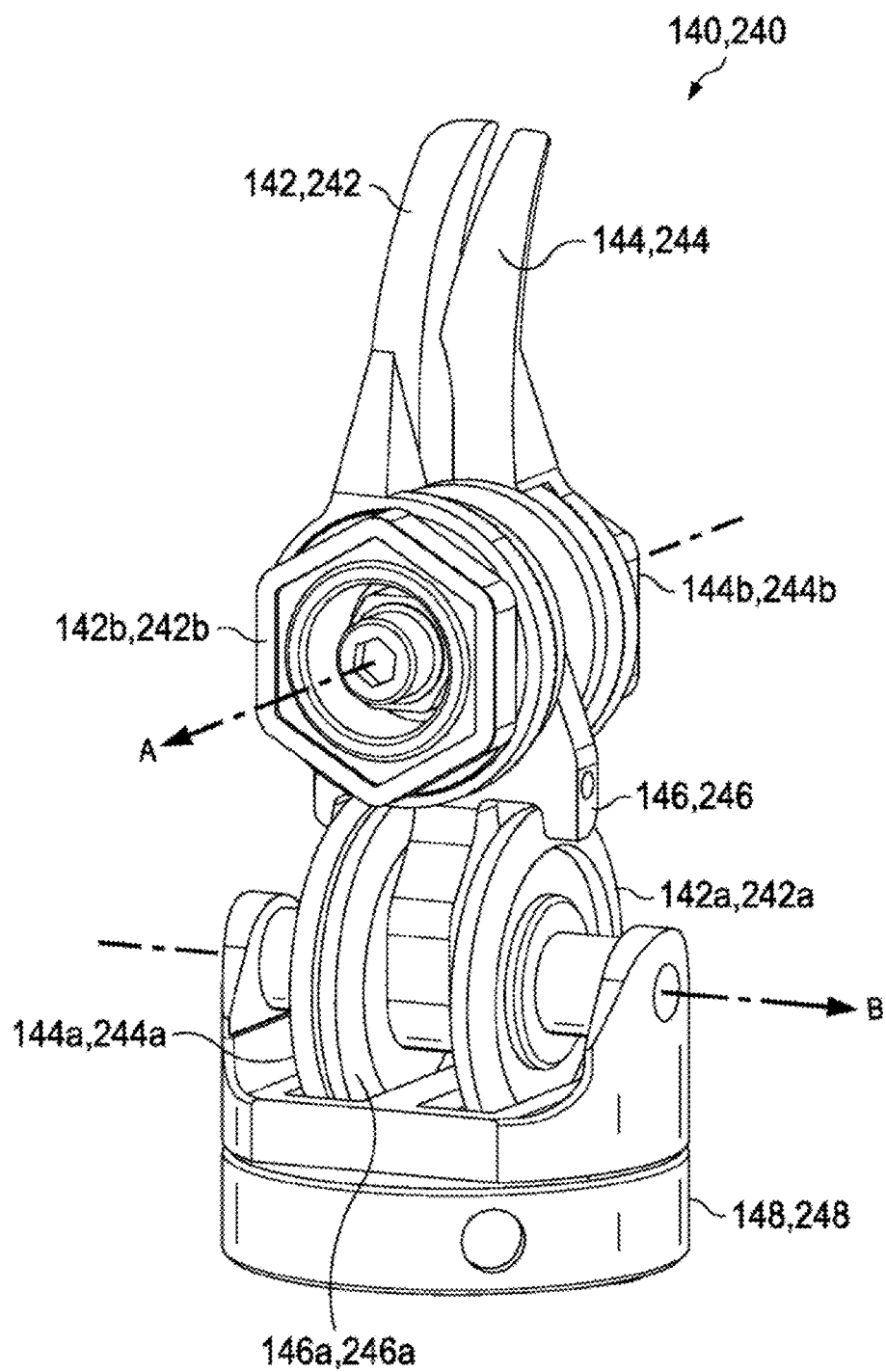
FIG. 8B is an illustration of a perspective view of an example embodiment of an end-effector assembly in the form of scissors.
Figure 8C:
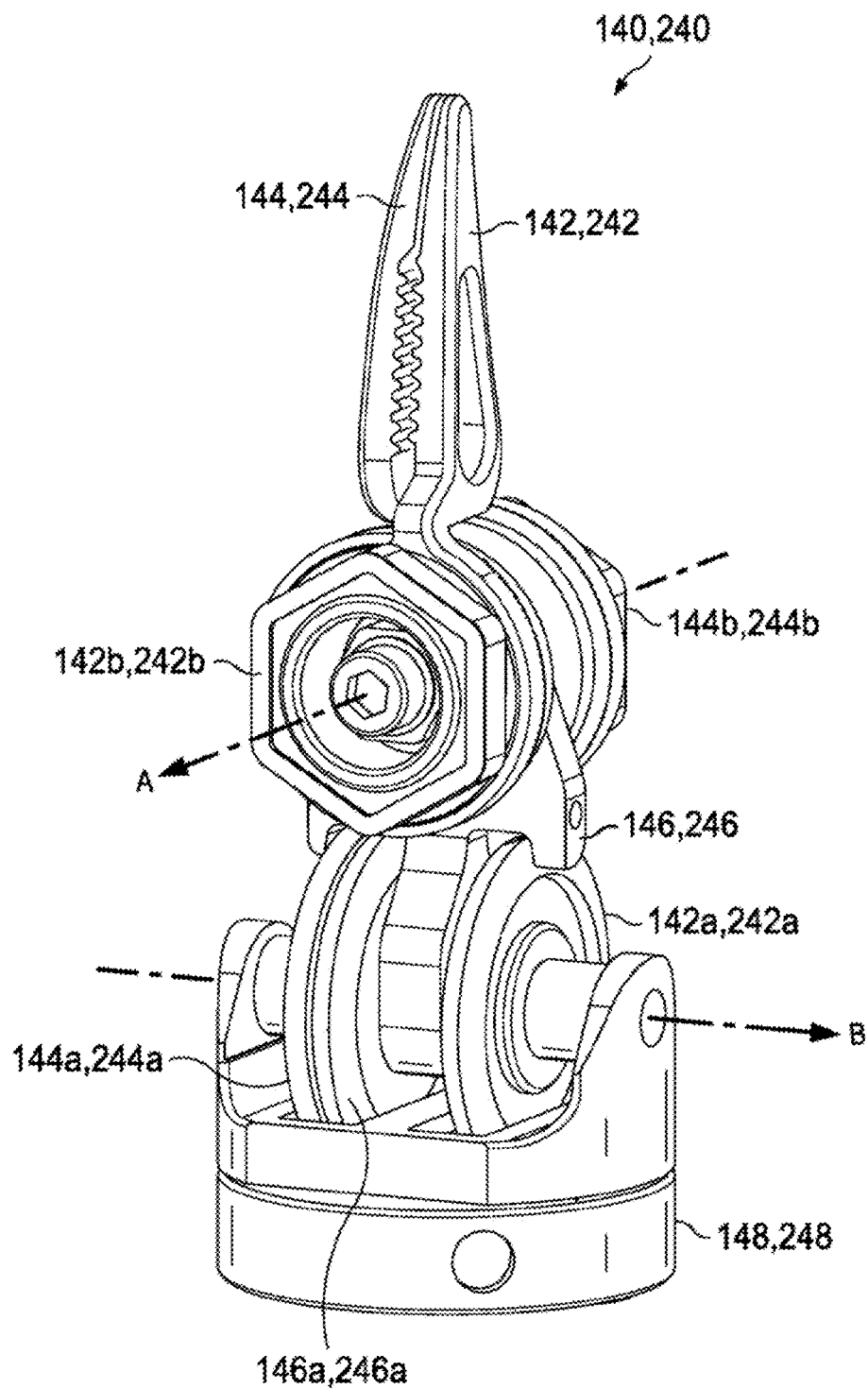
FIG. 8C is an illustration of a perspective view of an example embodiment of an end-effector assembly in the form of a grasper.

(iii) Cooperation of the First Instrument Assembly and Second Instrument Assembly In example embodiments, the first instrument (e.g., first instrument 142, 242) and second instrument (e.g., second instrument 144, 244) may be selectively moveable/drivable independently from one another. In example embodiments, the first instrument (e.g., first instrument 142, 242) and the second instrument (e.g., second instrument 144, 244) may be selectively moveable/drivable in a similar or same manner, such as being moveable/driveable at the same time, for the same duration, for the same distance, and/or with the same output energy. Although the figures illustrate end-effector assembly having a first instrument and a second instrument, it is to be understood in the present disclosure that the end-effector assembly may have more other instruments or may only have a first instrument or a second instrument without departing from the teachings of the present disclosure. For example, the first instrument (e.g., first instrument 142, 242) and the second instrument (e.g., instrument 144, 242) may cooperate to form a grasper, as illustrated in FIG. 8A. As another example, the first instrument (e.g., first instrument 142, 242) and the second instrument (e.g., instrument 144, 242) may cooperate to form scissors, as illustrated in FIG. 8B. As another example, the first instrument (e.g., first instrument 142, 242) and the second instrument (e.g., instrument 144, 242) may cooperate to form a Maryland grasper, as illustrated in FIG. 8C. Other forms and types of first instruments and/or second instruments are contemplated in the present disclosure in addition to or in replacement of the first instrument and/or second instrument described above and herein without departing from the teachings of the present disclosure.

For example, as described above, the first instrument (e.g., first instrument 142, 242) may be configurable to receive an electric current (e.g., first electric current) applied from a first energy source (not shown) so as to perform actions of an electrosurgical instrument. In addition to or in replacement, the second instrument (e.g., second instrument 144, 244) may be configurable to receive an electric current (e.g., second electric current) applied from a second energy source (not shown). The first current may be the same in magnitude as but opposite in direction to the second current in example embodiments, and the first energy source may be the same as or different from the second energy source in example embodiments. In such embodiments where the first instrument and second instrument collectively cooperate to form a monopolar electrosurgical instrument, or the like, when a mass (e.g., a tissue mass) is provided between the first instrument (e.g., first instrument 142, 242) and second instrument (e.g., second instrument 144, 244) and an electric current is applied to the first instrument (e.g., first instrument 142, 242) or the second instrument (e.g., second instrument 144, 244), the mass will serve to enable the applied electric current to pass through and aid in cutting, coagulating, desiccating, and/or fulgurating the mass. Similarly, in embodiments where the first instrument and second instrument collectively cooperate to form a bipolar electrosurgical instrument, or the like, when a mass (e.g., a tissue mass) is provided between the first instrument (e.g., first instrument 142, 242) and second instrument (e.g., second instrument 144, 244) and an electric current is applied to the first instrument (e.g., first instrument 142, 242) and the second instrument (e.g., second instrument 144, 244), the mass will serve to enable the applied electric current to pass through and aid in performing a surgical action, including cutting, coagulating, desiccating, cauterizing, and/or fulgurating the mass. Although the first instrument and/or second instrument may be described above and in the present disclosure to receive an electric current, it is to be understood that the first instrument and/or second instrument may also be configurable to receive a voltage potential, thermal energy, heat, cold temperature application, radiation, etc. to perform the said surgical action without departing from the teachings of the present disclosure.

(iv) Wrist Assembly

The wrist assembly may be securable or secured to the first instrument assembly in example embodiments. The wrist assembly may comprise a wrist driven portion (e.g., wrist driven portion 146a, 246a). The wrist assembly may further comprise a connector (e.g., connector 148, 248).

The wrist driven portion (e.g., wrist driven portion 146a, 246a) may be configurable to be driven by the wrist drive portion (e.g., wrist drive portion 136, 146) of the arm assembly (e.g., arm assembly 131, 231). The wrist driven portion (e.g., wrist driven portion 146a, 246a, as illustrated in at least FIGS. 3A, 4A, 5, 6, and 8A-C) may be driven by the wrist drive portion (e.g., wrist drive portion 136, 236) in such a way as to move the first instrument (e.g., first instrument 142, 242). For example, the wrist driven portion (e.g., wrist driven portion 146a, 246a) may be driven to move the first instrument (e.g., first instrument 142, 242) relative to a second axis (e.g., axis B, as illustrated in FIGS. 4-8). In this regard, such movement of the first instrument (e.g., first instrument 142, 242) may be a rotation of a distal end of the first instrument (e.g., first instrument 142, 242) relative to a point on the second axis (e.g., axis B), and such point may serve as a pivot for such movement. In addition to or in replacement, the wrist driven portion (e.g., wrist driven portion 146a, 246a) may be driven by the wrist drive portion (e.g., wrist drive portion 136, 236) in such a way as to move the second instrument (e.g., second instrument 144, 244). For example, the wrist driven portion (e.g., wrist driven portion 146a, 246a) may be driven to move the second instrument (e.g., second instrument 144, 244) relative to the second axis (e.g., axis B, as illustrated in FIGS. 4-8). In this regard, such movement of the second instrument (e.g., second instrument 144, 244) may be a rotation of a distal end of the second instrument (e.g., second instrument 144, 244) relative to a point on the second axis (e.g., axis B), and such point may serve as a pivot for such movement. In example embodiments, the wrist driven portion (e.g., wrist driven portion 146a, 246a) may be driven by the wrist drive portion (e.g., wrist drive portion 136, 236) in such a way as to collectively move the first instrument (e.g., first instrument 142, 242) and the second instrument (e.g., second instrument 144, 244). For example, the wrist driven portion (e.g., wrist driven portion 146a, 246a) may be driven to collectively move the first instrument (e.g., first instrument 142, 242) and the second instrument (e.g., second instrument 144, 244) relative to the second axis (e.g., axis B, as illustrated in FIGS. 4-8). In this regard, such movement of the first instrument (e.g., first instrument 142, 242) and the second instrument (e.g., second instrument 144, 244) may be a collective rotation of a distal end of the first instrument (e.g., first instrument 142, 242) and distal end of the second instrument (e.g., second instrument 144, 244) relative to a point on the second axis (e.g., axis B), and such point may serve as a pivot for such movement.

The wrist driven portion (e.g., wrist driven portion 146a, 246a) may be any mechanism, device, or the like, configurable to be driven by the wrist drive portion (e.g., wrist drive portion 136, 236). For example, the wrist driven portion (e.g., wrist driven portion 146a, 246a) may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one wrist driven portion, it is to be understood in the present disclosure that the end-effector assembly may have more than one wrist driven portions without departing from the teachings of the present disclosure.

Controller

In example embodiments, the surgical system 100, 200 may include a controller (or computing device, manipulator, and/or master input device). The controller may include one or more processors. The controller may be configurable to perform one or more of a plurality of operations in, on, and/or to the surgical system 100, 200. For example, the controller may be configurable to communicate with and/or control one or more elements of the surgical system 100, 200, such as the surgical arm assembly (e.g., surgical arm assembly 130, 230), the image capturing assembly 120, 220, etc. The controller may be accessible and/or controllable by the surgical team (e.g., via a user interface), and the surgical team may be able to communicate with and/or control the configuring and/or operation of the one or more elements of the surgical system 100, 200. For example, the controller may be configurable to control a movement and action of some or all parts of the surgical arm assembly (e.g., surgical arm assembly 130, 230). The controller may be configurable to receive, from the user interface (e.g. user interface 910), user interaction information (e.g., performed by the surgical team) representative of user interactions performed on the user interface (e.g., user interface 910). The controller may be further configurable to process the received user interaction information. The controller may be further configurable to transmit, based on the processing, one or more commands to the surgical arm assembly (e.g., surgical arm assembly 130, 230). The one or more commands transmitted may include commanding the first instrument drive portion (e.g., first instrument drive portion 132, 232) to drive the first instrument driven portion (e.g., first instrument driven portion 142a, 242a) in such a way as to cause a movement of the first instrument (e.g., first instrument 142, 242) in a first direction relative to a first axis (e.g., axis A). The one or more commands transmitted may also include commanding the wrist drive portion (e.g., wrist drive portion 136, 236) to drive the wrist driven portion (e.g., wrist driven portion 146a, 246a) in such a way as to cause a movement of the first instrument (e.g., first instrument 142, 242) in a second direction relative to a second axis (e.g., axis B). The second axis (e.g., axis B) may be different from the first axis (e.g., axis A).

In an example embodiment, the controller may be configurable to detect a resistance in a movement of at least a part of the end-effector assembly (e.g., end-effector assembly 140, 240) and communicate a haptic feedback response to the user interface (e.g., user interface 910).

The controller may also be configurable to receive one or more of a plurality of responses, feedback, actions, and/or measurements from one or more elements of the surgical system 100, 200 including, but not limited to, movements of one or more elements of the surgical system 100, 200, haptic feedback responses, and responses and/or measurements pertaining to position (including orientation), applied force, proximity, temperature, pressure, humidity, etc., of, by, and/or nearby to the surgical arm assembly (e.g., surgical arm assembly 130, 230).

In an example embodiment, the controller may be configurable to receive, from the user interface (e.g., user interface 910), user interactions (e.g., by the surgical team) performed on the user interface (e.g., user interface 910) representative of commanding an energy source (not shown) to apply an electric current (e.g., a first electric current) to the first instrument (e.g., first instrument 142, 242). In doing so, such electric current (e.g., first electric current) enables the first instrument (e.g., first instrument 142, 242) to perform the actions of an electrosurgical instrument. In example embodiments, when the controller receives, from the user interface (e.g., user interface 910), the user interactions performed on the user interface (e.g., user interface 910) representative of commanding the energy source to apply (or not apply) the electric current (e.g., first electric current) to the first instrument (e.g., first instrument 142, 242) to perform (or not perform) the actions of an electrosurgical instrument, the controller may be configurable to transmit a command to the energy source to apply (or not apply) the electric current to the first instrument (e.g., first instrument 142, 242). Furthermore, the controller may be configurable to apply (or not apply) an electric current to the second instrument (e.g., second instrument 144, 244) in a similar or same manner as the first instrument (e.g., first instrument 142, 242).

In an example embodiment, when the controller detects a resistance in a movement of at least a part of the end-effector assembly (e.g., end-effector assembly 140, 240), the controller may be configurable to determine the part of the end-effector assembly (e.g., end-effector assembly 140, 240) encountering the resistance. Furthermore, the controller may be configurable to provide a haptic feedback response to the user interface (e.g., user interface 910) based on such determining.

In example embodiments, the controller may be separate from the user interface (e.g., user interface 910). Alternatively, the controller may include a part or all of the user interface (e.g., user interface 910), or may communicate with a processor of the user interface (e.g., user interface 910).

User Interface (e.g., User Interface 910)

In example embodiments, the surgical system 100, 200 may include a user interface (e.g., user interface 910). The user interface (e.g., user interface 910) may be configurable for use by one or more operators (e.g., one or more members of the surgical team). The user interface (e.g., user interface 910) may be configurable to receive one or more of a plurality of user interactions from the one or more operators and command one or more elements of the surgical system 100, 200 to perform an action or prevent from performing an action. Such receiving may be via the controller and/or directly from the one or more elements of the surgical system 100, 200. For example, the user interface (e.g., user interface 910) may be configurable to control (e.g., via the controller) a movement of one or more parts of the surgical system 100, 200, such as the first instrument (e.g., first instrument 142, 242), second instrument (e.g., second instrument 144, 244), and other parts of the surgical arm assembly (e.g., surgical arm assembly 130, 230). The user interface (e.g., user interface 910) may also be configurable to (e.g., via the controller) enable the surgical arm assembly (e.g., surgical arm assembly 130, 230) to perform and/or disable the surgical arm assembly (e.g., surgical arm assembly 130, 230) from performing actions of an electrosurgical instrument. For example, the user interface (e.g., user interface 910) may be configurable to (e.g., via the controller) apply, control/regulate the applying of, and/or prevent the applying of an electric current (e.g., the first electric current and/or second electric current) to the first instrument (e.g., first instrument 142, 242) and/or second instrument (e.g., second instrument 144, 244).

The user interface (e.g., user interface 910) may also be configurable to receive one or more of a plurality of responses, feedback, actions, and/or measurements from one or more elements of the surgical system 100, 200 and/or the controller including, but not limited to, movements of one or more elements of the surgical system 100, 200, haptic feedback responses, and responses and/or measurements pertaining to position (including orientation), applied force, proximity, temperature, pressure, humidity, etc., of, by, and/or nearby to the surgical arm assembly (e.g., surgical arm assembly 130, 230).

In example embodiments, the user interface (e.g., user interface 910) may be separate from the controller. Alternatively, the user interface (e.g., user interface 910) may include a part or all of the controller, or may include a processor in communication with the controller.

In example embodiments, the surgical system 100, 200 may include a memory (not shown) in communication with the controller and/or user interface (e.g., user interface 910). The memory may be for use in storing information received from, processed by, and/or communicated to/from the controller and/or user interface (e.g., user interface 910).

The user interface (e.g., user interface 910) may also include one or more graphical interfaces (such as a monitor, projection system, etc.) for use in displaying video and/or audio content captured by an element of the surgical system 100, 200 (such as a camera arm assembly 120). The one or more graphical interfaces may also be for use in displaying some or all responses, feedback, actions, and/or measurements received from one or more elements of the surgical system 100, 200 and/or the controller including, but not limited to, movements of one or more elements of the surgical system 100, 200, haptic feedback responses, and responses and/or measurements pertaining to position (including orientation), applied force, proximity, temperature, pressure, humidity, etc., of, by, and/or nearby to the surgical arm assembly (e.g., surgical arm assembly 130, 230).

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, controller, manipulator, master input device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A surgical arm assembly comprising:
    an end-effector assembly having:
        a first instrument assembly having:
            a first instrument having a proximal end and a distal end; and
            a first instrument driven portion having a first instrument connection portion and a first instrument driven gear, the first instrument connection portion connecting the first instrument driven gear to the proximal end of the first instrument in such a way that, when the first instrument driven gear is driven to rotate, the distal end of the first instrument is driven to rotate relative to a first central axis; and
        a wrist assembly connected to the first instrument assembly, the wrist assembly having a wrist driven gear and a wrist body, the wrist body connecting the wrist driven gear to the first instrument assembly, and wherein, when the wrist driven gear is driven to rotate, the first instrument assembly is driven to rotate relative to a second central axis, the first central axis being orthogonal to the second central axis, the first central axis being non-coplanar to the second central axis; and
    an arm assembly having a wrist connector portion, a first integrated motor, and a second integrated motor, the arm assembly attachable to and detachable from the wrist assembly via the wrist connector portion, wherein, when the arm assembly is attached to the wrist assembly, the first instrument driven gear and the wrist driven gear are drivable to rotate by the first integrated motor and second integrated motor, respectively, and wherein, when the wrist connector portion is detached from the wrist assembly, the first instrument driven gear and the wrist driven gear are not drivable to rotate by the first integrated motor and second integrated motor, respectively.

2. The surgical arm assembly of claim 1, wherein the detaching of the wrist assembly from the arm assembly includes disconnecting the wrist body from the wrist connector portion, and wherein the attaching of the wrist assembly to the arm assembly includes connecting the wrist body to the wrist connector portion.

3. The surgical arm assembly of claim 1, further comprising:
a first instrument drive portion for use in connecting the first integrated motor and the first instrument driven gear, the first instrument drive portion configurable to drive the first instrument driven gear when the arm assembly is attached to the wrist assembly and when the first integrated motor drives the first instrument drive portion.

4. The surgical arm assembly of claim 1, wherein the arm assembly further includes:
a wrist drive portion connecting the second integrated motor and the wrist driven gear, the wrist drive portion configurable to drive the wrist driven gear when the arm assembly is attached to the wrist assembly and when the second integrated motor drives the wrist drive portion.

5. The surgical arm assembly of claim 1,
wherein the end-effector assembly further includes a second instrument assembly having:
a second instrument having a proximal end and a distal end; and
a second instrument driven portion having a second instrument connection portion and a second instrument driven gear, the second instrument connection portion connecting the second instrument driven gear to the proximal end of the second instrument in such a way that, when the second instrument driven gear is driven to rotate, the distal end of the second instrument is driven to rotate relative to the first central axis.

6. The surgical arm assembly of claim 5,
wherein the wrist assembly is connected to the second instrument assembly;
wherein the wrist body connects the wrist driven gear to the second instrument assembly; and
wherein, when the wrist driven gear is driven to rotate, the second instrument assembly is driven to rotate relative to the second central axis.

7. The surgical arm assembly of claim 5, wherein the arm assembly further includes:
a third integrated motor;
wherein, when the arm assembly is attached to the wrist assembly, the second instrument driven gear is drivable to rotate by the third integrated motor, and wherein, when the wrist connector portion is detached from the wrist assembly, the second instrument driven gear is not drivable to rotate by the third integrated motor.

8. The surgical arm assembly of claim 7, further comprising:
a second instrument drive portion connecting the third integrated motor and the second instrument driven gear, the second instrument drive portion configurable to drive the second instrument driven gear when the arm assembly is attached to the wrist assembly and when the third integrated motor drives the second instrument drive portion.

9. The surgical arm assembly of claim 5, wherein the first instrument and the second instrument are configurable to move independently from one another relative to the first central axis.

10. The surgical arm assembly of claim 5, wherein the wrist driven portion is configurable to collectively move the first instrument and the second instrument relative to the second central axis.

11. The surgical arm assembly of claim 5,
further comprising a second instrument insulative portion provided between the proximal end of the second instrument and the second instrument connecting portion, the second instrument insulative portion configured in such a way as to electrically isolate the second instrument from the rest of the second instrument assembly.

12. The surgical arm assembly of claim 1,
further comprising a first instrument insulative portion provided between the proximal end of the first instrument and the first instrument connecting portion, the first instrument insulative portion configured in such a way as to electrically isolate the first instrument from the rest of the first instrument assembly.

13. The surgical arm assembly of claim 12,
wherein the first instrument is configurable to further receive a first electric current applied from an energy source so as to perform the actions of an electrosurgical instrument;
wherein, when the first instrument receives the first electric current, the first instrument insulative portion is configured to electrically isolate the first electric current received by the first instrument from passing to other parts of the end-effector assembly.

14. The surgical arm assembly of claim 1,
wherein the surgical arm assembly is in communication with a user interface;
wherein the surgical arm assembly is configurable to provide a haptic feedback response to the user interface when one or more of the following occur:
a movement of the first instrument encounters a resistance;
a driving of the first instrument by the first instrument driven gear encounters a resistance;
a driving of the first instrument driven gear by the first instrument drive portion encounters a resistance;
a driving of the first instrument by the wrist drive portion encounters a resistance; and/or
a driving of the wrist driven gear by the wrist drive portion encounters a resistance.

15. A surgical arm assembly comprising:
an end-effector assembly having:
an instrument assembly having:
a first instrument having a proximal end and a distal end;
a second instrument having a proximal end and a distal end;
a first instrument driven portion, the first instrument driven portion configured in such a way as to drive the first instrument to rotate relative to a first central axis;
a second instrument driven portion, the second instrument driven portion configured in such a way as to drive the second instrument to rotate relative to the first central axis; and an arm assembly having a connector portion, a first integrated motor, and a second integrated motor, the arm assembly attachable to and detachable from the end-effector assembly via the connector portion, wherein, when the arm assembly is attached to the end-effector assembly:

the first instrument driven portion is drivable by the first integrated motor to drive the first instrument to rotate relative to the first central axis; and the second instrument driven portion is drivable by the second integrated motor to drive the second instrument to rotate relative to the first central axis.

16. The surgical arm assembly of claim 15, further comprising:

a first instrument drive portion for use in connecting the first integrated motor and the first instrument driven portion, the first instrument drive portion configurable to drive the first instrument driven portion when the arm assembly is attached to the end-effector assembly and when the first integrated motor drives the first instrument drive portion; and a second instrument drive portion for use in connecting the second integrated motor and the second instrument driven portion, the second instrument drive portion configurable to drive the second instrument driven portion when the arm assembly is attached to the end-effector assembly and when the second integrated motor drives the second instrument drive portion.

17. The surgical arm assembly of claim 16, wherein the surgical arm assembly is in communication with a user interface;

wherein the surgical arm assembly is configurable to provide a haptic feedback response to the user interface when one or more of the following occur:

a movement of the first instrument encounters a resistance;

a driving of the first instrument by the first instrument driven portion encounters a resistance;

a driving of the first instrument driven portion by the first instrument drive portion encounters a resistance;

a driving of the second instrument by the second instrument driven portion encounters a resistance; and/or a driving of the second instrument driven portion by the second instrument drive portion encounters a resistance.

18. The surgical arm assembly of claim 15, wherein the first instrument and the second instrument are configurable to move independently from one another relative to the first central axis.

19. The surgical arm assembly of claim 15, further comprising:

a first instrument insulative portion provided between the proximal end of the first instrument and the first instrument driven portion, the first instrument insulative portion configured in such a way as to electrically isolate the first instrument from the rest of the instrument assembly; and a second instrument insulative portion provided between the proximal end of the second instrument and the second instrument driven portion, the second instrument insulative portion configured in such a way as to electrically isolate the second instrument from the rest of the instrument assembly.

20. The surgical arm assembly of claim 19, wherein the first instrument is configurable to further receive a first electric current applied from an energy source so as to perform the actions of an electrosurgical instrument;

wherein, when the first instrument receives the first electric current, the first instrument insulative portion is configured to electrically isolate the first electric current received by the first instrument from passing to other parts of the end-effector assembly.

21. A surgical arm assembly comprising:

an end-effector assembly having:

a first instrument assembly having:

a first instrument having a proximal end and a distal end, the first instrument configurable to rotate relative to a first central axis; and a wrist assembly connected to the first instrument assembly, the wrist assembly having a wrist driven gear and a wrist body, the wrist body connecting the wrist driven gear to the first instrument assembly, and wherein, when the wrist driven gear is driven to rotate, the first instrument assembly is driven to rotate relative to a second central axis, the first central axis being orthogonal to the second central axis, the first central axis being non-coplanar to the second central axis; and an arm assembly having a wrist connector portion and a first integrated motor, the arm assembly attachable to and detachable from the wrist assembly via the wrist connector portion, wherein, when the arm assembly is attached to the wrist assembly, the wrist driven gear is drivable to rotate by the first integrated motor, and wherein, when the wrist connector portion is detached from the wrist assembly, the wrist driven gear is not drivable to rotate by the first integrated motor.

22. The surgical arm assembly of claim 21, wherein the detaching of the wrist assembly from the arm assembly includes disconnecting the wrist body from the wrist connector portion, and wherein the attaching of the wrist assembly to the arm assembly includes connecting the wrist body to the wrist connector portion.

23. The surgical arm assembly of claim 21, wherein the arm assembly further includes:

a wrist drive portion connecting the first integrated motor and the wrist driven gear, the wrist drive portion configurable to drive the wrist driven gear when the arm assembly is attached to the wrist assembly and when the first integrated motor drives the wrist drive portion.

24. The surgical arm assembly of claim 21, further comprising a first instrument insulative portion provided between the proximal end of the first instrument and the wrist assembly, the first instrument insulative portion configured in such a way as to electrically isolate the first instrument from the rest of the end-effector assembly.

25. The surgical arm assembly of claim 24, wherein the first instrument is configurable to further receive a first electric current applied from an energy source so as to perform the actions of an electrosurgical instrument;

wherein, when the first instrument receives the first electric current, the first instrument insulative portion is configured to electrically isolate the first electric current received by the first instrument from passing to other parts of the end-effector assembly.

26. The surgical arm assembly of claim 21,
wherein the surgical arm assembly is in communication with a user interface;
wherein the surgical arm assembly is configurable to provide a haptic feedback response to the user interface when one or more of the following occur:
  a movement of the first instrument encounters a resistance;
  a driving of the first instrument by the wrist drive portion encounters a resistance; and/or
  a driving of the wrist driven gear by the wrist drive portion encounters a resistance.

* * * * *